United States Patent
Bhuiyan

(10) Patent No.: US 12,170,147 B1
(45) Date of Patent: *Dec. 17, 2024

(54) GLAUCOMA DETECTION AND EARLY DIAGNOSIS BY COMBINED MACHINE LEARNING BASED RISK SCORE GENERATION AND FEATURE OPTIMIZATION

(71) Applicant: iHealthScreen Inc., Queens Village, NY (US)

(72) Inventor: Alauddin Bhuiyan, Queens Village, NY (US)

(73) Assignee: IHEALTHSCREEN INC., Queens Village, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/616,876

(22) Filed: Mar. 26, 2024

Related U.S. Application Data

(63) Continuation-in-part of application No. 18/219,433, filed on Jul. 7, 2023, now Pat. No. 11,941,809.

(51) Int. Cl.
*G16H 50/20* (2018.01)
*G06Q 10/1093* (2023.01)
*G06T 7/00* (2017.01)
*G06V 10/44* (2022.01)
*G06V 10/82* (2022.01)
*G06V 20/70* (2022.01)
(Continued)

(52) U.S. Cl.
CPC ......... *G16H 50/20* (2018.01); *G06Q 10/1095* (2013.01); *G06T 7/0012* (2013.01); *G06V 10/454* (2022.01); *G06V 10/82* (2022.01); *G06V 20/70* (2022.01); *G06V 40/18* (2022.01); *G16H 15/00* (2018.01); *G16H 50/30* (2018.01); *G06V 2201/03* (2022.01)

(58) Field of Classification Search
None
See application file for complete search history.

(56) References Cited

U.S. PATENT DOCUMENTS 8,787,638 B2    7/2014   Zee et al.
10,123,689 B2 *   11/2018   Jia ..................... G06T 7/0012
(Continued)

FOREIGN PATENT DOCUMENTS

CN      113011450 A    6/2021

*Primary Examiner* — Nancy Bitar
(74) *Attorney, Agent, or Firm* — George Likourezos; Carter, DeLuca & Farrell LLP

(57) ABSTRACT

Systems, methods, and computer program products for predicting and detecting the onset of retinal diseases are provided. A method of detecting glaucoma includes: pre-training at least one neural network model of a plurality of neural network models based on a small data classifier; training the plurality of neural network models based on a plurality of indications of glaucoma based on retinal data including at least two of a peripapillary atrophy value, a disc hemorrhage value, and a blood vessel structure analysis value; simultaneously generating a risk score associated with each of the plurality of indications based on the trained plurality of neural network models; combining the risk score associated with each of the plurality of indications based on a classification model to produce a likelihood of glaucoma; and determining whether glaucoma is present based on the likelihood of glaucoma.

19 Claims, 11 Drawing Sheets

(51) Int. Cl.
*G06V 40/18* (2022.01)
*G16H 15/00* (2018.01)
*G16H 50/30* (2018.01)

(56) References Cited

U.S. PATENT DOCUMENTS

| | | |
|---|---|---|
| 10,963,737 B2 * | 3/2021 | Odaibo ............... G06F 18/2413 |
| 11,080,850 B2 | 8/2021 | Cho et al. |
| 11,941,809 B1 * | 3/2024 | Bhuiyan ................ G16H 50/30 |
| 2011/0190657 A1 | 8/2011 | Zhou et al. |
| 2017/0169565 A1 | 6/2017 | Huang et al. |
| 2019/0191988 A1 | 6/2019 | Gargeya |
| 2021/0118525 A1 * | 4/2021 | Craig ..................... G16B 20/20 |
| 2022/0165418 A1 * | 5/2022 | Li ........................ G06T 7/0012 |
| 2022/0230300 A1 * | 7/2022 | Kawczynski ......... G06T 7/0004 |

* cited by examiner

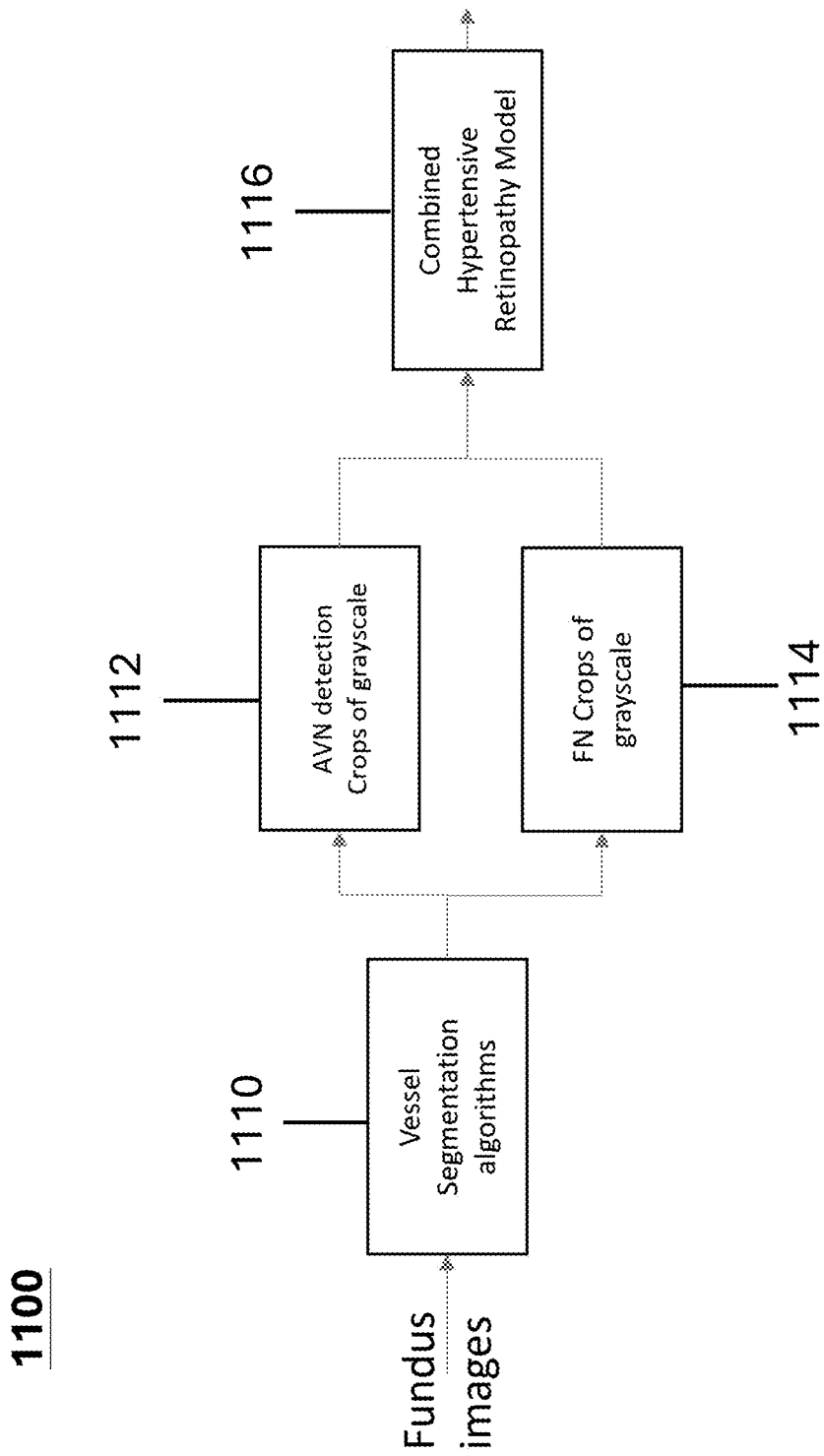

GLAUCOMA DETECTION AND EARLY DIAGNOSIS BY COMBINED MACHINE LEARNING BASED RISK SCORE GENERATION AND FEATURE OPTIMIZATION

CROSS-REFERENCE TO RELATED APPLICATIONS

This application is a continuation-in-part and claims the benefit of, and priority to, U.S. patent application Ser. No. 18/219,433, filed Jul. 7, 2023, the entire content of which are hereby incorporated by reference.

BACKGROUND

Glaucoma is a group of eye conditions that damage the optic nerve, the health of which is vital for good vision. This damage is often caused by an abnormally high pressure in your eye. Although scientists are unsure as to what causes the most common types of glaucoma, it has been found that many people with glaucoma have high eye pressure. Therefore, treatments that lower eye pressure may help to slow the disease. There's no way to prevent glaucoma. An eye exam may be used in order to detect glaucoma before it affects an individual's vision, but current techniques are unable to accurately, efficiently, and reliably detect such glaucoma in individuals. Therefore, there is a need to have a technique that allows for the accurate, efficient, and reliable prediction and detection of the onset of glaucoma.

SUMMARY

According to some embodiments of the present disclosure, methods of and computer program products for predicting and detecting the onset of glaucoma are provided. In various embodiments, a method of detecting glaucoma is provided. At least one neural network model of a plurality of neural network models may be pre-trained using a small data classifier. The plurality of neural network models may be trained based on a plurality of indications of glaucoma. A risk score associated with each of the plurality of indications may be simultaneously generated based on the trained plurality of neural network models. The risk score associated with each of the plurality of indications may be combined based on a classification model to produce a likelihood of glaucoma. A determination of whether glaucoma is present may be made based on the likelihood of glaucoma.

In various embodiments, a system is provided including a computing node comprising a computer readable storage medium having program instructions embodied therewith. The program instructions are executable by a processor of the computing node to cause the processor to perform a method. At least one neural network model of a plurality of neural network models may be pre-trained using a small data classifier. The plurality of neural network models may be trained based on a plurality of indications of glaucoma. A risk score associated with each of the plurality of indications may be simultaneously generated based on the trained plurality of neural network models. The risk score associated with each of the plurality of indications may be combined based on a classification model to produce a likelihood of glaucoma. A determination of whether glaucoma is present may be made based on the likelihood of glaucoma.

In various embodiments, a computer program product for backing up and restoring a managed cluster of nodes is provided including a computer readable storage medium having program instructions embodied therewith. The program instructions are executable by a processor to cause the processor to perform a method. At least one neural network model of a plurality of neural network models may be pre-trained using a small data classifier. The plurality of neural network models may be trained based on a plurality of indications of glaucoma. A risk score associated with each of the plurality of indications may be simultaneously generated based on the trained plurality of neural network models. The risk score associated with each of the plurality of indications may be combined based on a classification model to produce a likelihood of glaucoma. A determination of whether glaucoma is present may be made based on the likelihood of glaucoma.

In various embodiments, a risk score may be generated for each of multiple indications of glaucoma, such as a cup-disc ratio, rim-disc ratio, peripapillary atrophy, disc hemorrhage, blood vessel structure/fractal dimension, nasalness of blood vessels, and retinal entire image. Examples of cup-disc ratio may include binary cup-disc ratio as glaucoma vs. non-glaucoma, and a 3-class cup-disc ratio for glaucoma and non-glaucoma probability score. Detection of peripapillary atrophy may be achieved with a higher confidence using the Optimizing Small Datasets Problem-Domain-Specific Pre-Training (OSDP-DSPT) algorithm, described further below, as well as an independent peripapillary atrophy measure to determine a risk score associated with peripapillary atrophy. Disc hemorrhage may be assessed via the OSDP-DSPT algorithm as well as an independent disc hemorrhage measure. Each of the risk scores may be generated based on an output of a separate machine learning model, such as a deep learning model, a deep neural network, or the like, with the multiple indications as input to each of the the deep learning models. A classification model, such as a logistic model tree (LMT) may be used to combine each of the risk scores to produce a probability/likelihood risk score of glaucoma. This technique may achieve a substantially high accuracy for the detection of glaucoma. In aspects, 8 probability scores are combined as a featured vector, which the LMT classifies based on the samples of glaucoma and non-glaucoma.

In various embodiments, the technique described herein may break down a glaucoma screening task into multiple, such as three, individual problems in a type of divide and conquer approach. Each of the aforementioned models may learn the respective features that are relevant to glaucoma independent of other features. For example, the features may include glaucoma features such as peripapillary atrophy and disc hemorrhage versus fifteen different features of retinal pathologies such as drusen, hemorrhage, exudates, cotton wool spots, and the like. Such an approach may increase the accuracy of feature detection for whether glaucoma is or will be present.

In various embodiments, the techniques described herein may divide a main problem into subproblems, each of which is associated with a machine learning model that may be pre-trained and trained. The output of each machine learning model may be combined using a classification model, such as a LMT, which may output value(s) used to determine whether glaucoma is or will be present. In particular, the output of each model may be a prediction for a particular indication of glaucoma. The classification model may learn from predictions from the output of each model. The classification model may provide a probability/likelihood risk score of glaucoma. The risk score of glaucoma may act as a binary classifier, for example by comparing the risk score to a predetermined or dynamically set threshold. The threshold may be set in a way that is balanced and/or a clinically useful sensitivity and specificity.

In various embodiments, a glaucoma probability/likelihood risk score may be generated using a OSDP-DSPT algorithm and a disc hemorrhage model (DHM). In various embodiments, peripapillary atrophy may be detected using OSDP-DSPT and a peripapillary atrophy model and to generate the glaucoma probability/likelihood risk score.

In various embodiments, a disc nasalness based glaucoma probability/likelihood risk score may be generated using OSDP-DSPT and a retinal disc center 20 degree image. This may be combined with information regarding other indications of glaucoma which may be generated separately. In various embodiments. In various embodiments, a glaucoma probability/likelihood risk score may be generated from the vessel architecture, which may be analyzed by removing the disc area of a fundus image and considering the entire blood vessel structure.

BRIEF DESCRIPTION OF THE DRAWINGS

A better understanding of the features and advantages of the present disclosure will be obtained by reference to the following detailed description that sets forth illustrative aspects, in which the principles of the present disclosure are utilized, and the accompanying drawings of which:

FIG. 11 depicts an overall high-level architecture of another proposed pre-training technique and screening system according to various embodiments of the present disclosure.

DETAILED DESCRIPTION

Figure 1:
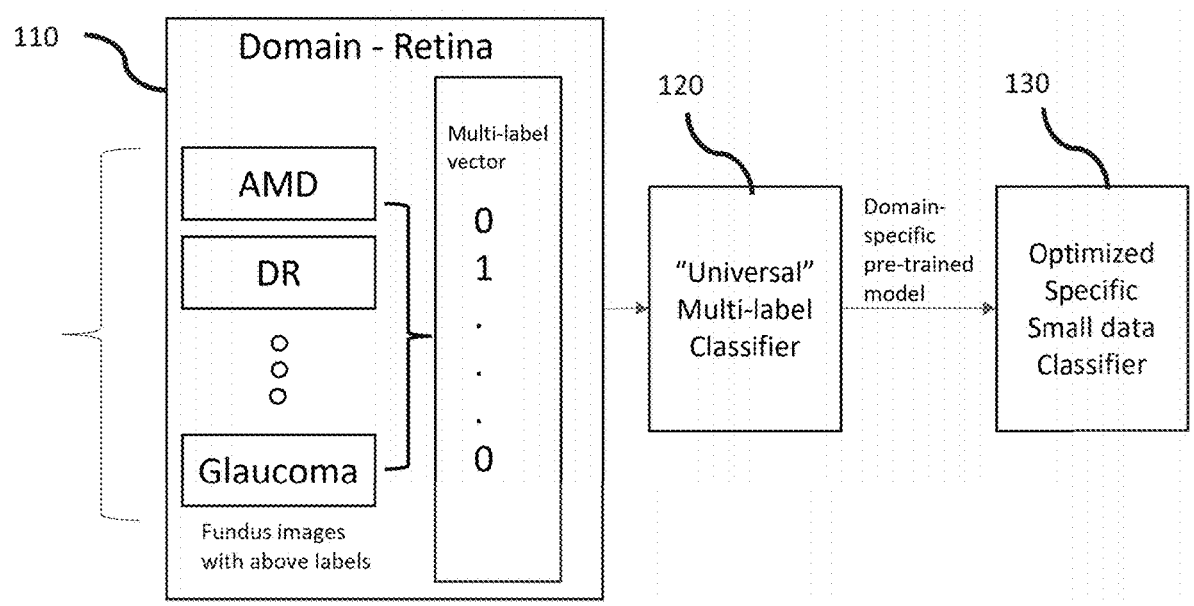
FIG. 1 depicts an overall high-level architecture of a proposed pre-training technique according to various embodiments of the present disclosure.

Glaucoma is a group of diseases that damage the eye's optic nerve and can result in vision loss and blindness. Glaucoma, with age-related macular degeneration (AMD) and diabetic retinopathy (DR), is one of the three leading causes of blindness in developed countries, and is now the second leading cause of blindness globally, after cataracts.

Glaucoma is characterized by loss of retinal ganglion cells (RGCs), which results in visual field impairment and structural changes to the retinal nerve fiber layer (RNFL) and optic disc. Glaucoma has few early symptoms. Over 3 million individuals in the United States have glaucoma, over 76 million individuals have glaucoma worldwide. It is projected that 111 million individuals will have glaucoma by the year 2040. About half of those affected do not know that they have glaucoma. In many cases, when glaucoma is detected, it is already too late, i.e., the case will involve an individual with irreversible visual field loss.

The social and economic costs of vision loss from glaucoma are very high. Early detection of conditions associated with glaucoma halts a downward spiral in overall health, which may be affect an individual because of the onset of: depression, loss of independence, need for nursing home care, falls, fractures, and death. These adverse outcomes are also extremely costly. The total economic burden of vision loss and blindness from all causes in the United States, including the direct and indirect costs, is now $145 billion, which is expected to triple by the year 2050 in real dollars, with increased longevity generally (Source: Prevent Blindness).

Therefore, there is a need to identify, at the early stages, individuals for treatment that have or that are suspected/prone to have glaucoma. Although glaucoma prediction/screening has been a focus area in medical research for many years, it is still difficult to diagnose, let alone predict, glaucoma with high degree of confidence. In particular, there is a lack of techniques or algorithms that present a more holistic approach in predicting and detecting or screening for the onset of glaucoma.

Recent studies have shown that retinal cup-disc ratio (CDR) may be highly correlated with glaucoma. The relationship between estimated RGC counts and CDR suggests that an assessment of change in CDR may be a sensitive method for the evaluation of progressive neural losses in glaucoma. Even relatively small changes in CDR may be associated with significant losses of RGCs, especially in eyes with larger CDRs, such as CDR>0.5. Enlarged CDR may be one indicator of the risk of glaucoma. Most individuals fall within an average vertical CDR of 0.4, and 2.5% of the population have a cup/disc ratio of over 0.7. In general, an eye with vertical CDR above 0.5 may be considered a glaucoma suspect and thus screening of the general population based on CDR may be highly effective for referral.

The medical imaging and diagnostics field has been revolutionized by advances in artificial intelligence (AI) and deep learning in recent years. Extensive research interest is being shown in using artificial intelligence for solving medical problems. For example, Ting et al. detailed the potential applications of AI in ophthalmology. Gulshan et al. showed the application of AI in diabetic retinopathy from fundus images using deep learning. There have been groundbreaking works published on late AMD prediction and diabetes screening in primary care settings. There is also considerable research in using deep learning in other medical areas such as multiple sclerosis, neurodegeneration and age-related macular degeneration.

Although several conventional AI techniques have been proposed to measure the cup-disc ratio, they have not been validated for screening individuals for glaucoma. Conventional research has focused on the detection of glaucoma, the disease itself, rather than the possible onset of glaucoma. For example, one conventional technique for glaucoma detection focused on using the standard Online Retinal fundus Image database for Glaucoma Analysis (ORIGA). This technique was proposed by Saxena et al. in 2020, which has a receiver operating characteristic (ROC) area under the curve (AUC) of 0.82.

Several of these studies with conventional techniques refer to glaucoma. To the extent that these studies refer to glaucoma, however, they do not differentiate the term glaucoma, a diagnosis of the disease that requires demonstrated structural and functional abnormalities, from glaucoma suspect, which is exactly what its name implies—a category or marker with an increased likelihood of disease that merits further investigation—i.e., a prediction of the onset of the disease. For example, in the ORIGA analysis described above, these terms are conflated, and the definition used for glaucoma, taken from ORIGA, is just C/D>0.65, which is purely structural, and which is inadequate for glaucoma diagnosis. Furthermore, the methodology in this ORIGA analysis is inadequate for deep learning, with only 90 images used for training. As another example, several of the other studies all have the stated goal of detecting glaucoma, by various means. However, this stated goal, by definition, would be too restrictive and not be appropriate for predicting, screening for, or detecting the onset of glaucoma.

Optimizing Small Datasets Problem-Glaucoma (Domain-Specific Pre-Training): OSDP-DSPT Algorithm The following describes the Optimizing Small Datasets Problem (OSDP) for Glaucoma, and more specifically the ODSP-Domain-Specific Pre-Training (DSPT) algorithm. Deep learning often requires an abundance of data. For example, in the medical field this data may include an abundance of medical images. However, the medical field, it may be rare to have such images to perform effective data science using traditional approaches. This is often the case for images of glaucoma-related abnormalities as well. For example, there is often a dearth of data available for disc hemorrhage, peripapillary atrophy and other lesions, and/or abnormalities. The novel techniques as described herein optimize machine learning techniques despite using small datasets. For example, such techniques described herein may be applied to glaucoma.

In various embodiments described herein, as much data as possible is collated in a specific domain of interest, such as glaucoma-related information and/or images. Then, all the available data that is collated is labeled in a multi-label fashion, such as by using a label vector or the like. This labeled data may be referred to as a "universal" dataset, and this may be used to train a multi-label classifier, which may be machine learning model(s), that can classify the dataset into not just multi-class but also multi-label. In particular, an intuition in performing such data processing may be that the relevant features in the specific domain may be learned by this "universal" multi-label classifier. Such a classifier may then be used as a "pretrained" machine learning model(s)/network, such as a neural network, to classify other images within the same specific domain of interest. Based on such pretraining, the classifier may have already learned the necessary and/or key features in the domain of interest, and higher level features may be learned in a new smaller dataset.

Using such an approach in the glaucoma domain an excellent classification model, as described herein, is achieved for an overall glaucoma detection system. In particular, in various embodiments described herein, machine learning models/sub-models may be enhanced by using such a "domain-specific pre-training" approach. For example, sub-models such as disc hemorrhage, peripapillary atrophy, and vessel analysis models may be enhanced by using such an approach.

As one example, nearly 500 thousand eye fundus images from various sources, such as AREDS, UKBiobank, SiMES, Kaggle-DR, etc., were used in a massive multi-label classification machine learning model. In this example, the labels used were all fundus abnormality related diseases classes such as diabetic retinopathy (DR), age-related macular degeneration (AMD), etc. During pre-training, multiple labels, such as 15 labels, were used to create a large multi-label fundus dataset. Fundus abnormalities such as microaneurysms, vessel abnormalities, cotton-wool spots, and hemorrhages were learned by a machine learning model in the pre-training step. The model also learned to ignore common artefacts, insignificant retinal patterns, lighting variations, and/or anomalies.

FIG. 1 depicts the overall high-level architecture of the proposed pre-training technique 100. In various embodiments described herein, FIG. 1 shows a general technique 100 for the development and/or pre-training of machine learning model(s) for use in the glaucoma domain. In various embodiments, technique 100 may be referred to as the ODSP-DSPT algorithm. Feature vector generator 110 may accept as inputs, information regarding fundus images, such as from the database(s) described herein. Each image may include a label that identifies one or more eye conditions, such as any fundus abnormality related disease in the fundus image. For example, the fundus images that are received as input by feature vector generator 110 may include labels such as AMD, DR, glaucoma, and/or the like. Using these input labels, feature vector generator 110 may generate one or more vectors for each image. For example, feature vector generator 110 may generate a multi-label vector that indicates the presence of and abnormality and/or other issue as seen in in an input fundus image using a value '1' and the absence of such an abnormality and/or other issue using a value '0'. This may be repeated for each label associated with each fundus image. Feature vector generator 110 may output one or more vectors, each associated with a fundus image, which include such binary values. The output of feature vector generator 110 may be input to a "universal" multi-label classifier 120. For example, feature vector generator 110 may accept 500 thousand fundus images each with 15 labels, as input, and may output a binary vector with 15 elements to multi-label classifier 120.

Multi-label classifier 120 may accept as input, one or more vectors from feature vector generator 110. Multi-label classifier 120 may use machine learning techniques to assign a single class label, out of several possible labels, to each vector that it receives from multi-label classifier 120. For example, multi-label classifier 120 may use a neural network, such as a deep neural network architecture, to classify and assign the single class label. The labels may be considered a "universal" label, which takes into account many possible eye conditions identified in fundus images. Thus, each fundus image input to feature vector generator 110 may have a "universal" label associated with it assigned by multi-label classifier 120. Multi-label classifier 120 may output the trained machine learning model and/or its properties, such as its weights, to optimized specific small data classifier 130. For example, multi-label classifier 120 may output a domain-specific, such a glaucoma-specific, pre-trained model and its properties to optimized specific small data classifier 130. This optimized specific small data classifier 130 may further process the input model that it receives, and it may generate a pre-trained machine learning model to be used by glaucoma screening system 200 and/or its constituent systems and processes.

Disc Hemorrhage Model (DHM)

In various embodiments described herein, machine learning model(s), such as a neural network that may be using a deep learning architecture, may be pre-trained with a dataset of eye fundus. In particular, the neural network may be pre-trained to detect one or more abnormalities in fundus images, for example, using datasets available to perform such pre-training. For example, this pre-training may include the use of general technique 100 for the development and/or pre-training of machine learning model(s) for use in the glaucoma domain. As one example, a deep machine learning architecture named "EfficientNet B5", was pre-trained with the "ImageNet" dataset. This dataset was implemented to train a neural network to detect the disc hemorrhages in fundus images. This dataset included 150 images with disc hemorrhages and 650 normal or without disc hemorrhages that were used to train and test the machine learning model.

The training dataset of eye fundus may first be processed, scaled, cropped, resized, transformed, and/or otherwise altered in order to reduce the number of retinal features encountered by the machine learning model(s). The sets of images within the dataset may be randomly or deterministically augmented, for example at each epoch, to produce variations in the dataset. For example, rotation, translation, and/or sheering with noise addition may be used to generate a new dataset containing such variations. During the training of the machine learning model(s), an early stopping mechanism for the training may be employed if no improvement in the error and/or training loss is observed in a predetermined number of epochs. In some instances, the stopping mechanisms may be employed if no improvement in the error and/or training loss is observed beyond a predetermined or dynamically changing threshold. The model(s) parameters with the least error and/or best training loss may be saved for future use. Another dataset may be used for validation and determination of accuracy of the trained machine learning model(s).

Continuing with the previous example of the neural network, "EfficientNet B5," full-color fundus images were first cropped using automated AI to get only the optic disc area of the retina. These images were then resized to 100×100 pixels. This cropping and resizing reduced the number of retinal features that the neural network encountered, given the relatively small amount of training data. The image sets were randomly augmented at each epoch for variation with rotation, translation and sheering with noise addition. This augmentation of the images resulted in newly generated images, which included up to 35 times the number of images as in the original number of images. An early stopping mechanism was employed wherein the training was stopped if no improvement in training loss is seen in 25 consecutive epochs. The network weights with the best training loss were saved. For external validation, another dataset obtained from the Department of Ophthalmology at Icahn School of Medicine at Mount Sinai was used. This validating dataset included 144 images with disc hemorrhage and 831 normal or without disc hemorrhages images. For detection of disc hemorrhage on the external validation dataset, 93.13% accuracy (95% CI: 91.35% to 94.64%) was achieved with a sensitivity of 71.53% (95% CI: 63.42% to 78.73%), a specificity of 96.87% (95% CI: 95.45% to 97.95%), and a kappa score of 0.71 (95% CI: 0.65 to 0.78).

Figure 2:
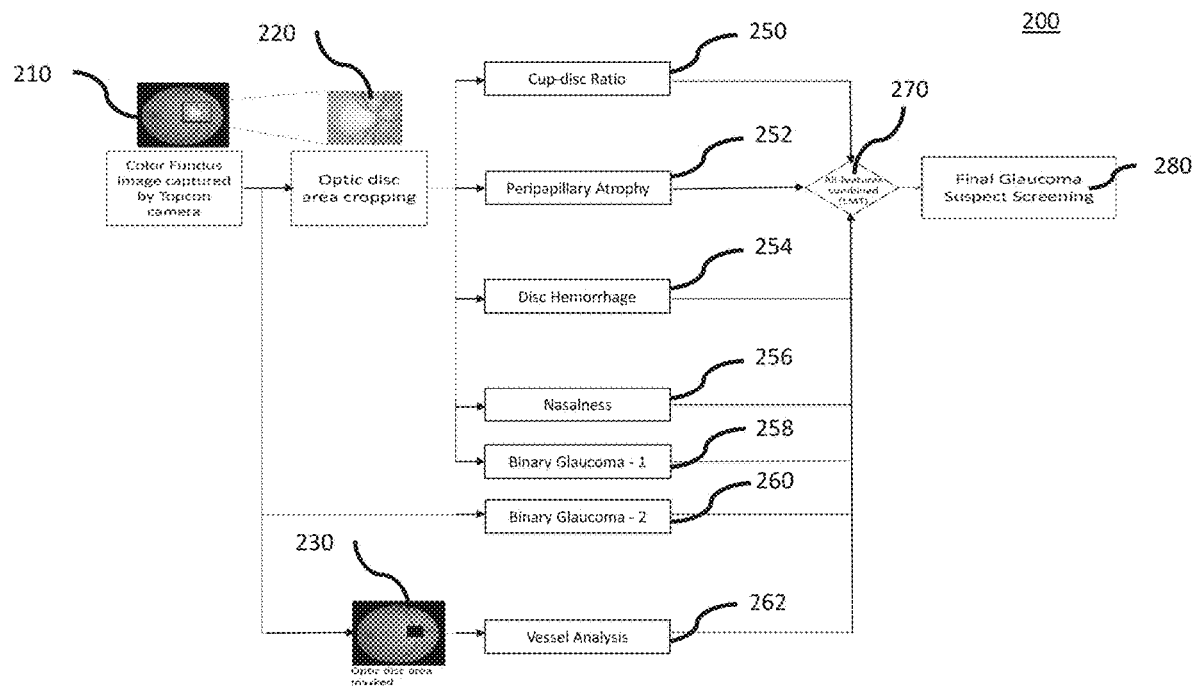
FIG. 2 depicts an example glaucoma screening system according to various embodiments of the present disclosure.

FIG. 2 depicts an example glaucoma screening system 200. This glaucoma screening system 200 is a solution made by iHealthscreen™. The system 200 may be used to screen individuals at risk of developing glaucoma and/or individuals at risk of having the disease worsening within them. The system 200 accepts as input eye fundus image, such as a fundus image for each eye of an individual. This input may be analyzed to automatically evaluate the features such as the cup-disc-ratio, the presence of peripapillary atrophy, disc hemorrhages, blood vessel pattern analysis, and/or the like. The system 200 may use machine learning model(s)/algorithm(s), such as deep neural network model(s), designed to evaluate a cumulative risk of glaucoma based on these features. The system 200 may them provide a final output, such as a binary output, indicating whether an individual is at risk of glaucoma or not, and/or to what extent the individual is at risk. As such, the system and its output may be used for glaucoma screening of an individual.

FIG. 2 shows a technical overview of the constituent parts of the glaucoma screening system 200. In general, as can be seen in FIG. 2, the system 200 combines multiple deep learning as well as traditional machine learning model(s) and approaches to build an accurate glaucoma screening system based on input fundus image(s). In particular, glaucoma screening system 200 of FIG. 2 includes a camera sensor 210, optic disc cropping system 220, image masking system 230, a cup-to-disc ratio estimation system 250, a peripapillary atrophy detection system 252, a disc hemorrhage detection system 254, nasalness system 256, a first binary classifier system 258, a second binary classifier system 260, a vessel analysis system 262, and a logistic model tree classifier 270, and a final glaucoma screening component 280.

Camera sensor 210 may be any suitable image and/or video capture device that may be able to capture fundus images from an individual. For example, camera sensor 210 may be fundus cameras available from Welch Allyn, Digisight, Volk, Topcon, Zeiss, Canon, Nidek, Kowa, CSO, CenterVue, Ezer, Optos and/or the like. Camera sensor 210 may capture fundus image(s) and may provide the image(s) to optic disc cropping system 220 and to image masking system 230.

Optic disc cropping system 220 may crop the fundus image(s) that it receives. Optic disc cropping module 220 may additionally or alternatively process, scale, resize, transform, and/or otherwise alter the image(s) that it receives. In various embodiments, optic disc cropping system 220 may reduce the number of retinal features in the fundus image(s) that it receives by performing one or more alterations to the image(s). This reduction in retinal features may be advantageous when the image(s) are processed by machine learning model(s), such as the machine learning model(s) used by the cup-to-disc ratio estimation system 250, the peripapillary atrophy detection system 252, the disc hemorrhage detection system 254, the nasalness system 256, the first binary classifier system 258, the second binary classifier system 260, the vessel analysis system 262, and/or the logistic model tree classifier 270.

Optic disc masking system 230 may mask the optic disc area in the fundus image(s) that it receives. For example, optic disc masking system 230 may mask the optic disc area that may be cropped by optic disc cropping system 220.

The cup-to-disc ratio estimation system 250 may take the retinal disc and/or macula center image or cropped disc center image(s) as input and returns the high cup-to-disc ratio probability or glaucoma probability and the binary value of the glaucoma subject or normal.

The peripapillary atrophy detection system 252 may take the retinal disc and/or macula center image or cropped disc center image as input and returns the probability of presence of peripapillary atrophy or the subject's glaucoma probability and the binary value of the glaucoma subject or normal.

The disc hemorrhage detection system 254 may take the retinal disc and/or macula center image or cropped disc center image as input and returns the probability of presence of disc hemorrhage probability and the subject's glaucoma probability and the binary value of the glaucoma subject or normal.

In various embodiments, each of the the cup-to-disc ratio estimation system 250, the peripapillary atrophy detection system 252, the disc hemorrhage detection system 254, and the nasalness system 256 may be pre-trained using the technique, such as the general technique 100 for the development and/or pre-training of machine learning model(s), described with reference to FIG. 1.

The nasalness system 256 may take the retinal disc and/or macula center image as input and returns the nasalness probability as output which is a significant risk factor for glaucoma.

The first binary classifier system 258 may take the retinal disc and/or macula center image as input and returns the glaucoma probability and binary value of the glaucoma subject or normal.

The second binary classifier system 260 may take the retinal disc and/or macula center image as input and returns the glaucoma probability without the disc area and binary value of the glaucoma subject or normal.

The vessel analysis system 262 may take the retinal disc and/or macula center image as input and returns the glaucoma probability without the disc area and binary value of the glaucoma subject or normal.

The logistic model tree (LMT) classifier 270 may receive the outputs of each of the each of the cup-to-disc ratio estimation system 250, the peripapillary atrophy detection system 252, the disc hemorrhage detection system 254, the nasalness system 256, the first binary classifier system 258, the second binary classifier system 260, and the vessel analysis system 262 and may combine these outputs to produce a probability/likelihood risk score of glaucoma. LMT considers one or multiple parameters through its function to determine the glaucoma or non-glaucoma. For example, logistic model tree (LMT) classifier 270 may be used to combine each of the risk scores that it receives as input to produce a probability/likelihood risk score of glaucoma. The LMT classifier 270 may output its result to final glaucoma screening component 280. Final glaucoma screening component 280 may make a determination of whether glaucoma is and/or will be present based on the probability/likelihood of glaucoma that it receives. Final glaucoma screening component 280 may also output the indications and/or risk scores associated with the cup-to-disc ratio estimation system 250, the peripapillary atrophy detection system 252, the disc hemorrhage detection system 254, the nasalness system 256, the first binary classifier system 258, the second binary classifier system 260, and/or the vessel analysis system 262. This output may be used to indicate the significance or risk associated with each of the associated abnormalities of the eyes.

Figure 3:
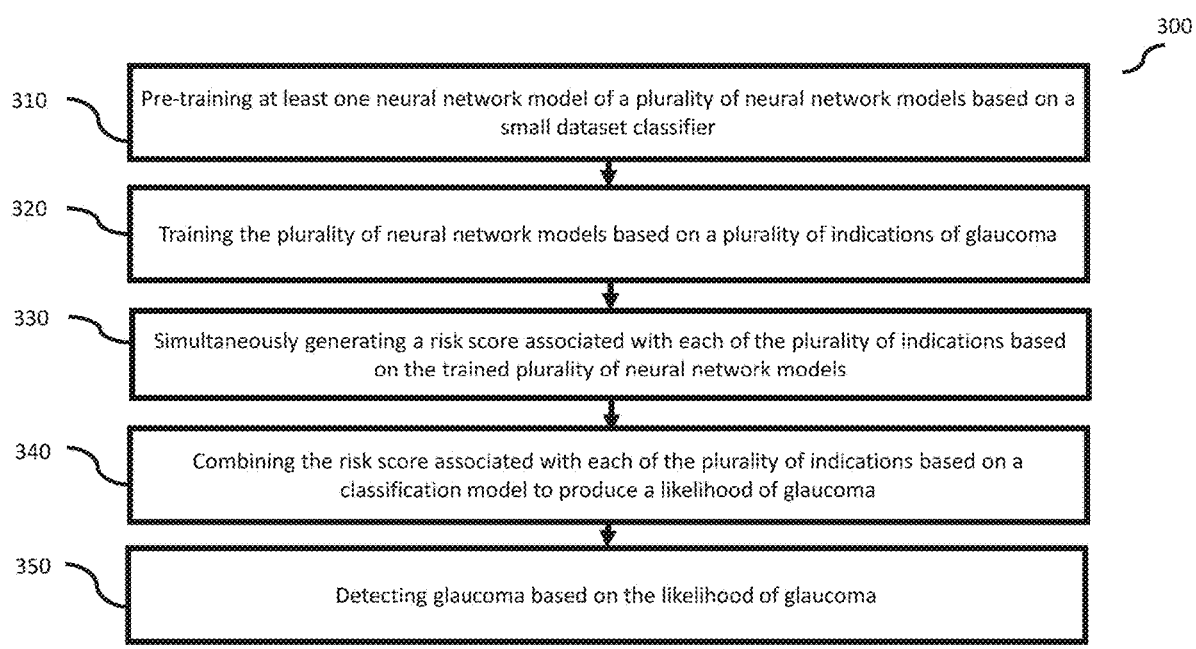
FIG. 3 is a flow diagram of an example process of detecting glaucoma according to various embodiments of the present disclosure.

FIG. 3 is a flow diagram of an example process of detecting glaucoma according to various embodiments of the present disclosure. At 310, at least one neural network model of a plurality of neural network models may be pre-trained using a small data classifier. At 320, the plurality of neural network models may be trained based on a plurality of indications of glaucoma. At 330, a risk score associated with each of the plurality of indications may be simultaneously generated based on the trained plurality of neural network models. At 340, the risk score associated with each of the plurality of indications may be combined based on a classification model to produce a likelihood of glaucoma. At 350, a determination of whether glaucoma is present may be made based on the likelihood of glaucoma. Based on the likelylihood or probability and the samples, a glaucoma and non-glaucoma or normal class is determined through a cutoff value.

EfficientNet Architecture for Individual feature based Glaucoma Risk Probability Generation The EfficientNet [1] architecture uses a model scaling technique for neural networks performing deep learning tasks. The EfficientNet architecture uses a simple yet highly effective compound coefficient to scale up convolutional neural networks (CNNs) in a more structured manner. Unlike conventional approaches that arbitrarily scale network dimensions, such as width, depth and resolution, this technique uniformly scales each dimension with a fixed set of scaling coefficients. The compound scaling technique used by EfficientNet is based by the intuition that if the input image is bigger, then the network needs more layers to increase the receptive field and more channels to capture more fine-grained patterns on the bigger image.

Any neural network architecture may be used with the methods and systems for predicting and detecting the onset of glaucoma described herein. For example, in addition to or instead of EfficentNet, the architectures associated with Inception, Resnet, Xception, and/or the like may be used. For these methods and systems, for the experiments described herein, a version of EfficientNet architecture known as "EfficientNetB4" was used. This architecture includes 19.5 million parameters, and a depth of 258 layers. Using the ImageNet dataset, the architecture achieved 82.9% accuracy (top-1) and 96.4% accuracy (top-5).

Through experimentations, such as what is describes in the examples below, it was determined that "EfficientNetB4" achieved efficient learning without the pitfalls of higher inference time, memory usage, and/or slower response times. After experimentation, as compared to the architectures used by Inception, Resnet and Xception, "EfficientNetB4" appeared to be the best architecture the prediction of glaucoma.

iPredict Glaucoma Screening System

Figure 7:
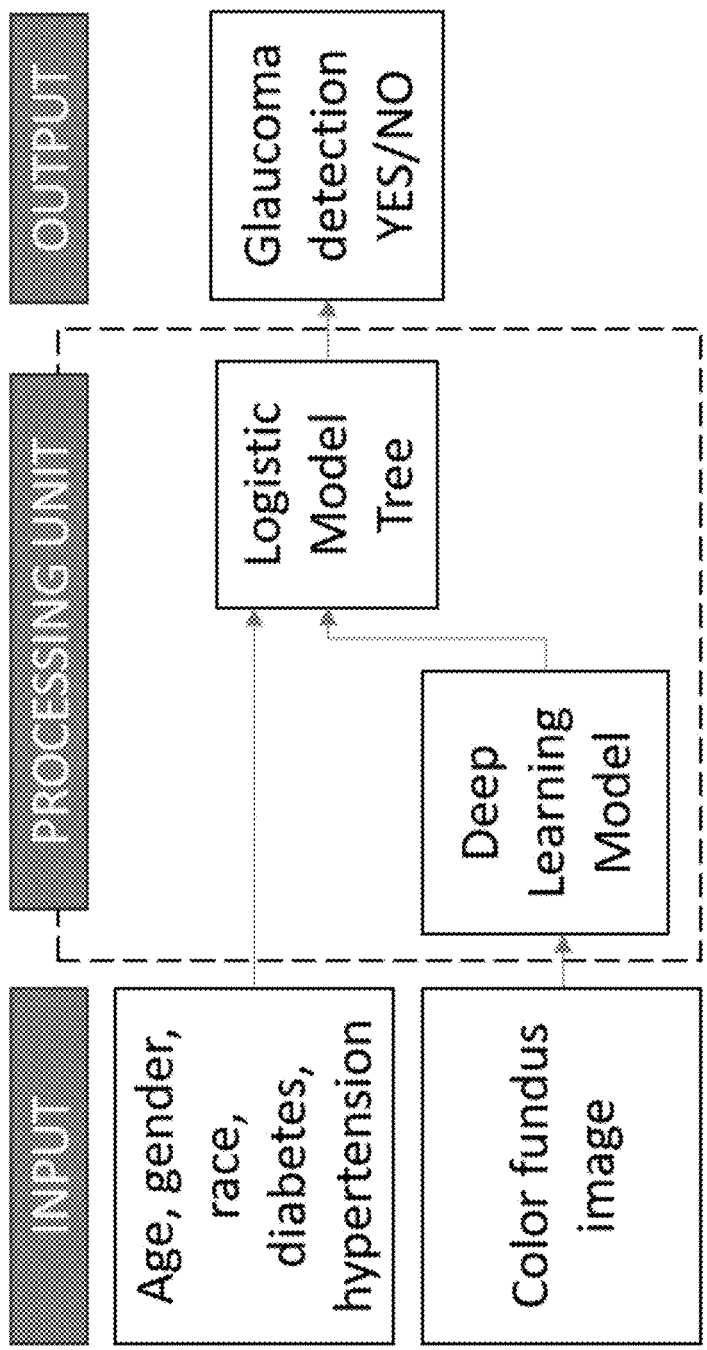
FIG. 7 depicts an overall high-level architecture of a proposed pre-training technique and screening system according to various embodiments of the present disclosure.
Figure 8:
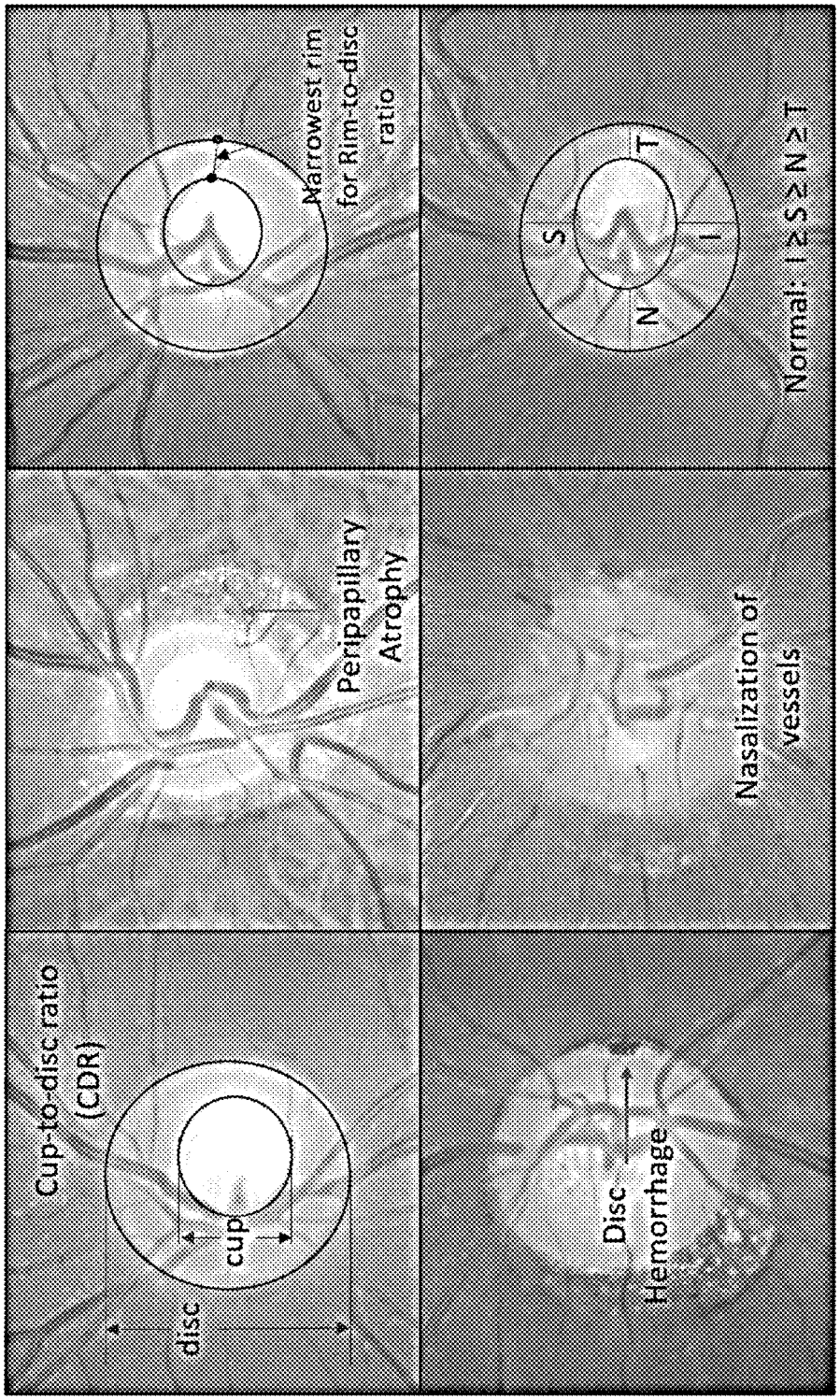
FIG. 8 depicts multiple indications of glaucoma according to various embodiments of the present disclosure.

FIG. 7 depicts an example glaucoma screening system 700. This glaucoma screening system 200 is a solution made by iHealthscreen™. The system 700 may be used to screen individuals at risk of developing glaucoma and/or individuals at risk of having the disease worsening within them. System 700 uses multiple indications of glaucoma such as cup-disc ratio (binary cup-disc ratio as glaucoma vs. non-glaucoma and 3-class cup-disc ratio for glaucoma and non-glaucoma probability score), rim-to-disc ratio, peripapillary atrophy, disc hemorrhage, blood vessel structure/fractal dimension, nasalness of blood vessels, retinal entire image (for binary glaucoma), to generate risk scores (FIG. 8). A probability score of having glaucoma based on each of the parameters or phenotypes is generated, and based on these scores, the best combinations of features and probabilities are selected (and probabilities were combined as a vector) through the LMT (LMT equation's produced threshold value 80% or above, established in diagnostics field of research) is considered a glaucoma subject.

System 500 breaks down the development of the glaucoma detection/screening tasks into 3 individual problems in a divide-and-conquer approach: (1) The individual models learn the respective features independent of other features (the features associated with glaucoma, e.g., peripapillary atrophy/disc hemorrhage, etc. vs. 15 different features of retinal pathologies such as drusen, hemorrhage, exudates, cotton wool spots, and so on), thereby increasing the accuracy of the feature detection. A deep learning model using 500K labeled retinal images on various pathologies or diseases may be used as a transfer learning platform to achieve a high accuracy model on a small dataset; (2) learn the probability of glaucoma presence or absence based on each feature; and then (3) combine them using the LMT. The accuracy and robustness may be demonstrated with external validation on 2 datasets: UK BioBank and ORIGA-light, and achieved consistent accuracy of 92.55% and 94.29%, respectively (Table 9). Sensitivity, specificity, and other accuracy measures are given along with their 95% confidence intervals.

The iPredict Glaucoma Detection Model employs system 500. Automated Glaucoma Detection using Color Fundus Imaging and Socio-demographic parameters (age, gender, and race) and traditional glaucoma risk factors (diabetes and hypertension) will be working as follows. First, the retinal image (disc and macular centers) will be taken using a color fundus camera. Second, the retinal disc and macular center images and the socio-demographic and glaucoma risk parameters will be input to the automated glaucoma screening model for processing (FIG. 7, processing step). User credentials will be needed to access the iPredict tool to utilize the automated glaucoma detection model. Finally, The glaucoma detection model will provide the output as a .pdf report with the glaucoma diagnosis results For example, if Glaucoma is detected, a report may be produced and/or the system may make an automatic and/or immediate referral to glaucoma specialist; if glaucoma is not detected, the system may automatically schedule a re-screen within a designated period of time (e.g., 12 months after the day when the screening took place). In aspects, the system may permit the user to select a date for re-screening based on manual input, profile preferences, or the like.

Figure 9:
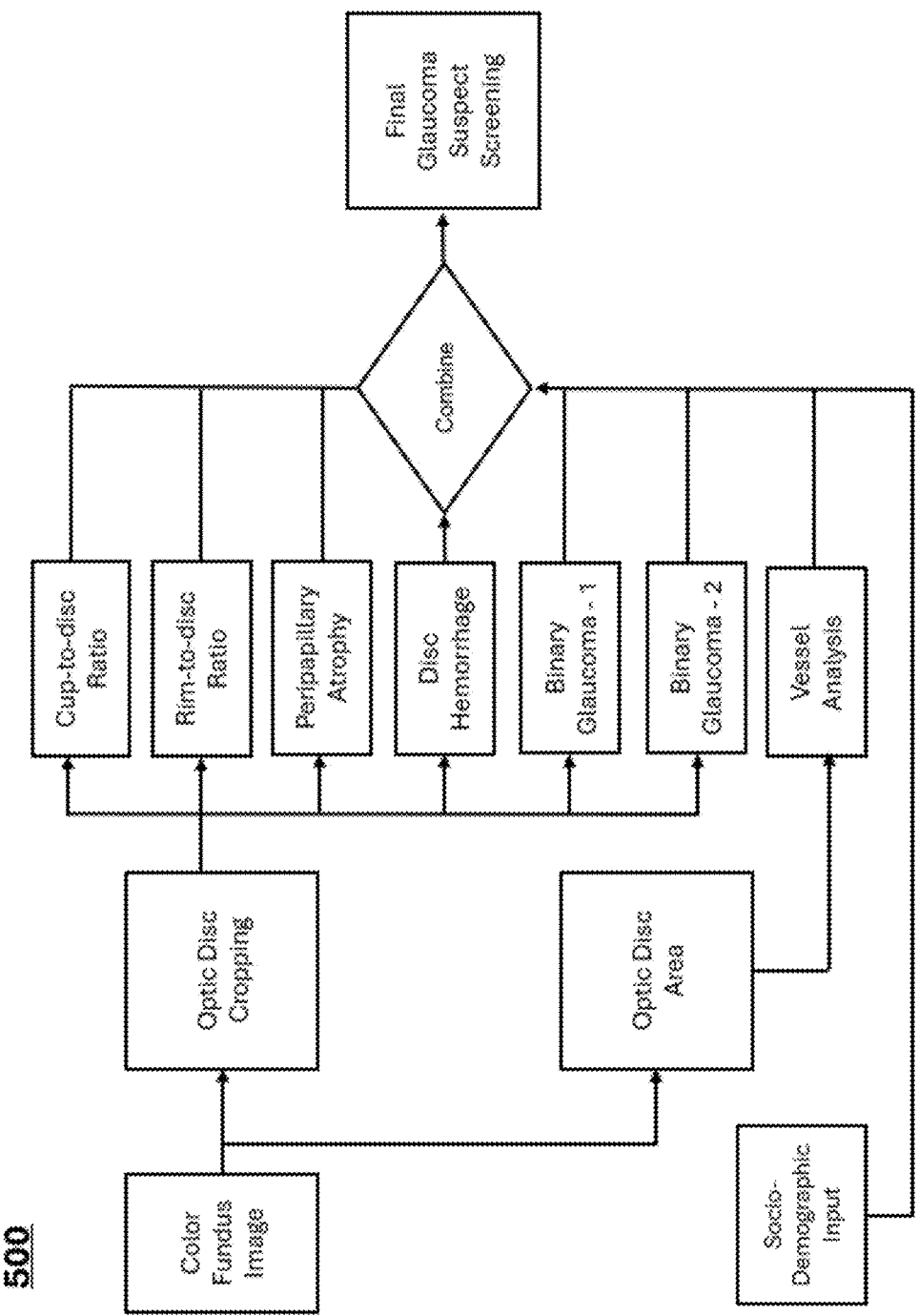
FIG. 9 depicts a flow diagram including the components of FIG. 7, according to various embodiments of the present disclosure.

Automated Glaucoma Detection Algorithm: First, the deep ML model determines the glaucoma features (cup-disc-ratio (CDR), rim-disc-ratio, peripapillary atrophy, vessel nasalization, overall blood vessel, and disc hemorrhage) if present, from the color fundus image. Second, for each of the features, the ML model determines the probability scores of glaucoma and non-glaucoma (LMT model is trained to find the individual feature-based glaucoma detection). Third, the image-based features are combined using LMT to determine the overall probability of glaucoma. Individual feature-based probability scores of glaucoma and non-glaucoma are utilized to combine and generate the overall probability score for glaucoma or non-glaucoma. Finally, the image-based features, and/or socio-demographic parameters (age, gender, and race), and traditional glaucoma risk factors (diabetes and hypertension) are combined as a feature vector (FIG. 9). The best combinations of features and probabilities (through the feature optimization by LMT) are selected (and probabilities were combined as a feature vector) through the LMT. Finally, the LMT equation produces one probability score for glaucoma, and the threshold value of 80% or above (the value established in the diagnostics field of research) is considered a glaucoma subject. A platform-independent code and cloud-based platform may be used to employ technique 500 in clinical settings.

FIG. 9 discloses glaucoma risk factor identification and glaucoma detection using color fundus imaging (Datasets used: AREDS and REFUGE to train/test the models; UK Biobank and ORIGA-Light for external validation). The imaging, measurements, and methods are described in detail below.

Cup Disc Ratio (CDR) Measurement

First, an artificial intelligence-based CDR (FIG. 8) grading system may be utilized. The network architectures incorporated may include Inception-Resnet V2, NasNet, Xception, and Inception. Deep learning architectures like Alexnet and VGG networks initially focused on stacking layers deeper and deeper, hoping to get better performance. The version used herein—Inception V3—uses RMSProp optimizer, factorized 7×7 convolutions, and added batch normalization in the auxiliary classifiersThe latest architecture is used. For example, for each model, generated probability scores classified the CDR below 0.4, between 0.4 and 0.6, and 0.6 and above which are combined by using the LMT, to generate the final results. In aspects, 1-3 continuous probability values are generated indicating CDR below 0.4, between 0.4 and 0.6, and/or 0.6 and above. External validation results for CDR detection (achieved accuracy above 84.92% with a sensitivity of 82.79% and specificity of 86.21% on the CDR above 0.6% detection; total images 315). Similarly based on the above 0.6 CDR, the glaucoma yes/no model through LMT, developed utilizing the REFUGE and AREDS dataset, and external validation is performed using the ORIGA-light and UK Biobank datasets (Table 1).

Disc Hemorrhage Detection Method

Disc hemorrhage (FIG. 8) is a feature of glaucomatous optic neuropathy commonly observed in low-pressure glaucoma and rarely found in normal eyes. A deep machine learning architecture named "EfficientNet B5" may be utilized and pre-trained with the "ImageNet" dataset, which may be implemented to train a network to detect the disc hemorrhages in fundus images. For this, 150 images with disc hemorrhages and 650 normal or without disc hemorrhages may be used to train and test the model. For external validation, another dataset obtained from the Department of Ophthalmology at Icahn School of Medicine at Mount Sinai may be utilized. This dataset consists of 144 images with disc hemorrhage and 831 normal or without disc hemorrhages. In addition, the deep learning model disclosed above may be used. The scores may be combined using LMT. Using AREDS, SiMES, IDRID, and REFUGE datasets, disc hemorrhage and no disc hemorrhaged images may be graded. For example, two ophthalmologists graded 4309 images selected from the datasets, which were further categorized as glaucoma, glaucoma suspects, and glaucoma features, including disc hemorrhage. An adjudication was performed if there was a disagreement between the graders on image grading. For the training total, positive images were 287, and the total negative (no disc hemorrhages) were 860 images. External validation was performed on 979 images with 181 disc hemorrhage images (accuracy of 91.08% with a sensitivity of 82.64% and specificity of 92.54%, as a feature). In aspects, at least 1 continuous probability value is generated indicating presence of disc hemorrhages. Table 9 shows the external validation of glaucoma detection accuracy based on disc hemorrhage.

Peripapillary Atrophy

Peripapillary atrophy (PPA) (FIG. 8) is a clinical finding associated with chorioretinal thinning and disruption of the retinal pigment epithelium (RPE) in the area surrounding the optic disc. The deep learning architecture discussed above may be used. The grading policy may be implemented similarly to disc hemorrhage. Datasets used-IDRID, ORIGA-light, and REFUGE for the Training dataset. For example, the total number of positive images was 294, and the number of negative images was (no pp atrophy) 600 (randomly selected). From a data obtained from the New York Eye and Ear Infirmary (with the 2 ophthalmologist gradings), the external validation was performed. The peripapillary atrophy detection accuracy was achieved above 95.4% (sensitivity 93.1% and specificity 97.6%). The peripapillary atrophy presence was used in LMT (using AREDS and REFUGE datasets) to detect the glaucoma and non-glaucoma subjects. In aspects, at least 1 continuous probability value is generated indicating the presence of atrophy. Table 1 shows the glaucoma detection results (external validation: accuracy 72.05% in UK Biobank and 75.71% in ORIGA-Light).

Rim-to-Disc Detection

The rim-to-disc ratio (FIG. 8) measurement method offers an approach similar to the CDR measurement. For example, four groups of rim-disc ratio may be determined from glaucoma and non-glaucoma subjects, and dividing the rim-disc ratio within four quartiles. For this, a semi-automated rim-disc ratio were measured using a Matlab tool. A total 400 images were used. Then based on the four quartiles, we trained the model with high rim-disc ratio (yes/no) using the deep learning framework depicted in FIG. 4 (accuracy 85.3 Then, the high rim-disc ratio score is used in the glaucoma detection model using the LMT model for glaucoma/non-glaucoma (trained with the REFUGE and AREDS dataset). %). In aspects, at least 1 continuous probability value is generated indicating a rim-to-disc ratio less than 0.1. The external validation results using UK Biobank and ORIGA-Light are shown in Table 9.

Vessel Nasalness

Vessel Nassalness (FIG. 8) as absent and present may be labeled and used to train the model with deep ML and based on this the glaucoma yes/no model may be developed through LMT. For example, 500 images may be taken from REFUGE, and AREDS datasets (achieved the nasalness detection accuracy 95%), to train the model based on the nasalness to detect the glaucoma (and the accuracy in Table 9).

Vessel Model

The vessel model may use blood vessel information without the disc area. The vessel model may model the vessel density and structure to detect glaucoma. In aspects, at least one continuous probability value is generated indicting an overall vessel analysis model. The direct image may be used for glaucoma and non-glaucoma classification. The experiment is shown in the Table 9.

Combined Features in LMT Model

FIG. 9 shows the overall glaucoma detection model utilizing the image-based parameters and socio-demographic and glaucoma risk factors. The model was trained using only the image-based features from the REFUGE and AREDS datasets. Also, trained on the image+socio-demographic (age, gender, and race) and glaucoma risk factors (diabetes and hypertension) using the AREDS dataset. The LMT model utilized a combination of color retinal image-based and other parameters' probability scores and optimized the probability scores to build the feature vector to classify glaucoma and non-glaucoma with high accuracy. For example, the LMT may be employed to take 8 input variables from the prior models and generate a final risk score. The external validation was performed in the UK Biobank and ORIGA-Light datasets, and the results are shown in Table 9 (for individual parameters, combined image-based parameters, and combined image-based, sociodemographic and glaucoma risk factors).

Papilledema Screening System

The following describes a screening system for papilledema, and more specifically the iHealthScreen™ screening detection system and method for papilledema. The papilledema detection system is an AI-based system designed to detect papilledema from fundus images, which are pictures of the back of the eye. Papilledema occurs when the optic nerve swells, usually due to increased pressure in the skull, and is a critical condition that can indicate serious health problems.

This system employs artificial intelligence, specifically machine learning, to analyze eye images. The system is trained on hundreds of images from large health datasets, learning to differentiate between normal eyes and those with signs of papilledema. The goal is for the AI to identify potential cases of papilledema efficiently. The training process involved using images from the AREDS, SiMES, and UK Biobank studies, ensuring a broad range of data. The system's performance is measured in terms of sensitivity, specificity, and overall accuracy, indicating how well it can identify true positives, true negatives, and its general reliability in diagnosis. Such a tool is invaluable in clinical settings. It allows for rapid screening of fundus images, highlighting cases that require closer examination by an ophthalmologist. This fast-tracks the identification and treatment of patients with papilledema, potentially saving lives by catching critical conditions early.

Figure 10:
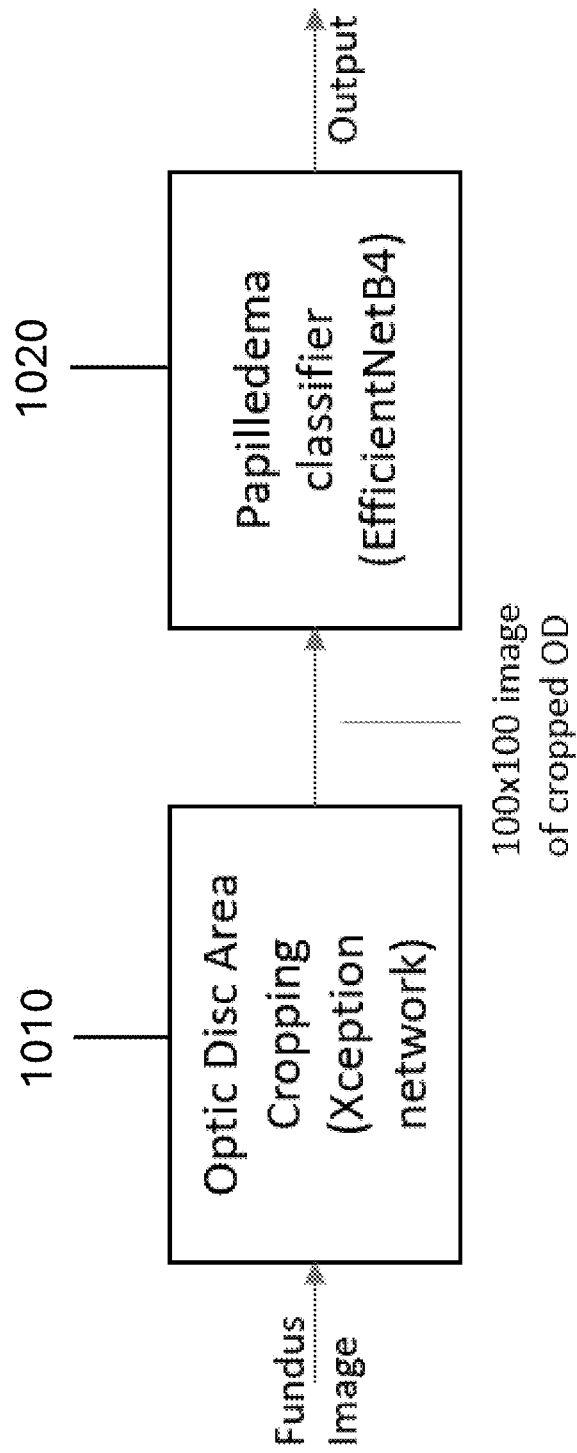
FIG. 10 depicts an overall high-level architecture of another proposed pre-training technique and screening system according to various embodiments of the present disclosure.

FIG. 10 depicts an example papilledema screening system 1000. The system includes two sequential modules: an optic disc area cropping module 1010 based on the Xception network, and a papilledema classification module 1020 utilizing the EfficientNetB4 architecture.

Datasets

Several datasets have been pivotal for training and testing the performance of machine learning models. The Age-Related Eye Disease Study (AREDS) dataset comprises 308 images, offering a rich source of data for identifying the markers of papilledema. Similarly, the Singapore Malay Eye Study (SiMES) provides 199 images, and the UK Biobank contributes an additional 238 images. These datasets are instrumental in developing algorithms capable of recognizing the subtle nuances and variations present in fundus images indicative of papilledema. The diversity and size of these datasets play a crucial role in enhancing the algorithm's accuracy and its ability to generalize across different populations.

For the validation of these AI models, a specific set of clinical trial images has been used, consisting of 20 positive (indicative of papilledema) and 40 normal images. This validation set is crucial for assessing the real-world applicability and reliability of the AI detection systems. By testing the models against this set, researchers can evaluate the sensitivity and specificity of their algorithms in distinguishing between normal variations in fundus images and those alterations caused by papilledema. This step is essential for ensuring that the AI-based detection systems can be confidently used in clinical settings, providing a quick and accurate diagnosis that can guide further management and treatment of the condition.

Module 1: Optic Disc Cropping (Xception Network)

The objective is to accurately locate and crop the region of the fundus image containing the optic disc. The architecture includes the Xception network, known for its depthwise separable convolutions, which offer an efficient model architecture. The process includes the following: (1) the fundus images are input to the Xception network; (2) the network processes these images to identify the optic disc's location; and (3) once the optic disc is localized, the image is cropped to focus solely on this region, ensuring that subsequent analysis is targeted and efficient.

Module 2: Papilledema Classification (EfficientNetB4)

The objective is to classify the cropped optic disc image as either showing signs of papilledema or not. The architecture includes EfficientNetB4, which is part of the EfficientNet family known for balancing model scaling in terms of depth, width, and resolution. The input size for this module is a standardized 100×100 pixel image, which is the cropped optic disc area obtained from Module 1. The process includes: (1) the cropped images of the optic disc, resized to 100×100 pixels, are fed into the EfficientNetB4 network; (2) the network utilizes its convolutional layers, batch normalization, and depthwise separable convolutions to analyze the features of the optic disc; (3) the final layers of the network, typically consisting of dense layers and a softmax activation, output a probability distribution over two classes: 'Papilledema' and 'No Papilledema'; and (4) the class with the highest probability is chosen as the model's prediction. In aspects, the probability distribution includes one or more risk scores associated with indications of Papilledema, similar to the risk scores for indications of glaucoma. In aspects, the system may use neural network(s) such as deep learning neural network models, convolutional neural networks (CNNs), and the like.

Training and Evaluation

The model requires a labeled dataset of fundus images, with annotations for the optic disc and labels indicating the presence or absence of papilledema. Both modules are trained separately. Module 1 is trained to optimize for accurate optic disc localization, while Module 2 is trained to classify the presence of papilledema accurately. Common metrics like accuracy, sensitivity, and PPV are used to evaluate the performance of the papilledema classification module.

Results

The sensitivity of the system 1000, which indicates its ability to correctly identify cases of papilledema, stands at 85.00%, with a 95% confidence interval (CI) ranging from 62.11% to 96.79%. This high sensitivity suggests that the system is quite effective in detecting true positive cases. On the other hand, the specificity, which measures the system's ability to correctly identify normal cases without papilledema, is reported at 82.50%, with a 95% CI between 67.22% and 92.66%. This indicates a strong capability of the system to correctly dismiss non-papilledema cases, minimizing false positive results. Furthermore, the overall accuracy of the system, which reflects its ability to correctly classify both positive and negative cases, is recorded at 83.33%, with a 95% confidence interval from 71.48% to 91%. This accuracy rate signifies that the system is reliably consistent in its performance across various test images (Table 10).

Hypertensive Retinopathy Screening System

The following describes a screening system for hypertensive retinopathy, and more specifically the iHealthScreen™ screening detection system and method for hypertensive retinopathy. In recent years, the application of artificial intelligence (AI) in healthcare has demonstrated significant potential in enhancing diagnostic accuracy and efficiency. Among various healthcare applications, the use of AI for the diagnosis and monitoring of hypertensive retinopathy presents a promising avenue. Hypertensive retinopathy, a condition characterized by changes in the retina due to high blood pressure, can lead to severe visual impairment if not diagnosed and treated promptly. Traditional methods for diagnosing hypertensive retinopathy rely heavily on the expertise of ophthalmologists, who examine fundus images for signs of the condition. However, these methods can be subjective and vary based on the clinician's experience.

This system introduces a novel AI-based model designed to automate the detection and grading of hypertensive retinopathy using fundus images. By leveraging advanced machine learning techniques, including convolutional neural networks (CNNs), the system aims to analyze fundus photographs with high accuracy and consistency, surpassing traditional diagnostic methods. The system is trained on a large dataset of annotated fundus images, encompassing a wide range of hypertensive retinopathy cases. This training enables the system to learn intricate patterns and anomalies associated with the condition, facilitating precise identification and grading of hypertensive retinopathy.

The system not only contributes to the body of knowledge on applying AI in ophthalmology but also offers a scalable and efficient tool for healthcare professionals. By automating the detection process, the system can assist ophthalmologists in making more informed decisions, potentially improving patient outcomes. Furthermore, it opens the door to more accessible screening for hypertensive retinopathy, particularly in regions with limited access to specialized healthcare services.

FIG. 11 depicts an example hypertensive retinopathy screening system 1100. The system takes in fundus images as input, which are processed using vessel segmentation algorithms 1110. Three methods are available: arteriovenous nicking (AVN) detection 1112, focal narrowing (FN) detection 1114, and combined AVN and FN detection 1116 on an external dataset.

AVN Detection

The process for arteriovenous nicking (AVN) detection 1112 involves three primary steps: (1) segmentation of the vessels; (2) crops of various regions in grayscale; and (3) running inference models on the crops. Vessel segmentation, vessel region mapping, and/or cropped grayscale images may be used for classification.

Initially, the blood vessels in the fundus images were segmented to isolate the arterial and venous structures. This step was crucial for accurately identifying areas where arteriovenous nicking could occur. Following segmentation, specific regions of interest (ROIs) around the vessels were cropped in grayscale. This approach facilitated a more focused analysis by the inference models. The final step involved running advanced inference models on the cropped regions to identify signs of AVN. These models of system 1100 were trained to detect subtle changes in the vessel structure indicative of hypertensive retinopathy.

Focal Narrowing Detection

The process for focal narrowing detection 1114 mirrors the approach used for AV Nicking detection: (1) segmentation of the vessels; (2) crops of various regions in grayscale; and (3) running inference models on the crops. Vessel segmentation, vessel region mapping, and/or cropped grayscale images may be used for classification.

First, as with AVN detection, vessel segmentation was performed to identify arterial and venous structures within the fundus images. Then, areas around the vessels were cropped in grayscale to highlight potential sites of focal narrowing. Finally, inference models specifically trained to recognize signs of FN analyzed the cropped images. These models of system 1100 assessed changes in vessel diameter that are characteristic of FN.

Combined AVN+FN Detection On An External Dataset

For a comprehensive hypertensive retinopathy model, both AVN and FN detections were combined. The process for combined AVN and FN detection 1116 involves two steps: (1) detection of either AVN or FN; and (2) thresholds based on probability of AVN or FN detection.

First, the model evaluated fundus images for the presence of either condition, using the previously described steps for AVN and FN detection. Vessel segmentation, vessel region mapping, and/or cropped grayscale images may be used for classification. Next, decisions on hypertensive retinopathy presence were made based on calculated probabilities for AVN and FN, using predetermined thresholds to improve diagnostic accuracy.

In aspects, one or more risk scores associated with indications of hypertensive retinopathy may be generated and/or combined, similar to the risk scores for indications of glaucoma.

Results

The AVN model demonstrated high efficacy in detecting AV Nicking, with notable sensitivity and specificity. The positive and negative predictive values, along with the positive and negative likelihood ratios, underscored the model's diagnostic precision. However, it's important to note that the disease prevalence indicated in the dataset does not reflect general hypertensive retinopathy prevalence (Table 11).

Like AVN detection, the focal narrowing detection showed strong sensitivity and specificity. The model's performance, indicated by its predictive values and likelihood ratios, highlights its potential utility in diagnosing hypertensive retinopathy through FN detection (Table 12).

When tested on an external dataset, the combined hypertensive retinopathy model exhibited excellent sensitivity and specificity. These results, particularly the positive and negative predictive values, demonstrate the model's robustness and reliability in diagnosing hypertensive retinopathy (Table 13). It's crucial to consider that the disease prevalence in the external dataset might not be representative of the general population.

The results suggest that AI-based models are highly effective in detecting hypertensive retinopathy features in fundus images, offering a promising tool for early diagnosis and management of this condition.

EXAMPLES

Data used as well as the experimental results as related to the models used by the methods, systems, and computer program products discussed herein are described in the Examples below. However, these Examples are only for illustrative purposes, and the data used as well as the experimental results as related to the present invention is not limited to the specific Examples mentioned below in any way.

Table 1 shows information regarding data from the UK Biobank. This data is also discussed in Appendix A included herein.

TABLE 1

| UK Biobank Data |
|---|
| Number of glaucoma patients (overall) - 9198 |
| Number of fundus images of glaucoma patients - 301 |
| Number of images whose CDR identified as 0.6 and above by the system - 127 |
| Number of images identified as 0.4 to 0.6 - 82 |
| Number of images below 0.4 - 92 |
| Number of images with peripapillary atrophy, as graded by the peripapillary identification system - 39 |
| Number of images with disc hemorrhages (identified with DR hemorrhage system) - 12 |

Example 1

Peripapillary Atrophy Experiments

Tables 2A and 2B show datasets used for peripapillary atrophy experiments and results of the peripapillary experiments respectively. Some of the datasets are also discussed in Appendix A included herein.

TABLE 2A

| Datasets Used for Peripapillary Atrophy Experiments |
|---|
| Datasets used - IDRID, ORIGA-light and REFUGE |
| Training dataset |
| Number of positive images - 294 |
| Number of negative images (no pp atrophy) - 600 (randomly selected) |
| Test |
| Number of positive images - 42 |
| Number of normal images - 42 |

TABLE 2B

| Results of Peripapillary Atrophy Experiments | | |
|---|---|---|
| Statistic | Value | 95% CI |
| Sensitivity | 93.18% | 81.34% to 98.57% |
| Specificity | 97.67% | 87.71% to 99.94% |
| Positive Predictive Value | 97.62% | 85.51% to 99.65% |
| Negative Predictive Value | 93.33% | 82.43% to 97.66% |
| Accuracy | 95.40% | 88.64% to 98.73% |

From the prospective trial data, using the peripapillary atrophy model described herein, there were 43 images classified as images with peripapillary atrophy. The images were saved separately.

Example 2

Results on CDR

Table 3A shows the results of CDR experiments. Tables 3B and 3C show validation results from mixed datasets as well as external datasets, respectively. Table 3D shows sensitivity and specificity for CDR values of 0.6 and above. Some of the datasets are also discussed in Appendix A included herein. The model described herein categorizes the images in 3 classes—CDR values below 0.4, CDR values between 0.4 and 0.6, and CDR values 0.6 and above. While the training dataset was built using AREDS, ORIGA-light and REFUGE, the experimental results shown here are from the prospective trial.

TABLE 3A

CDR Results

Training dataset (mixed group)
CDR < 0.4 – 1000
0.4 < CDR < 0.6 – 390
0.6 < CDR – 600

TABLE 3B

CDR Validation results from the mixed dataset (AREDS, ORIGA-light & REFUGE)

| Actual | Predicted CDR < 0.4 | Predicted 0.4 < CDR < 0.6 | Predicted 0.6 < CDR |
|---|---|---|---|
| CDR < 0.4 | 34 | 3 | 4 |
| 0.4 < CDR < 0.6 | 3 | 24 | 1 |
| 0.6 < CDR | 4 | 6 | 72 |

Weighted Kappa=0.785
Kappa=0.772
SE of kappa=0.046
95% confidence interval: From 0.682 to 0.861

TABLE 3C

CDR External validation results (from the prospective trial)

| Actual | Predicted CDR < 0.4 | Predicted 0.4 < CDR < 0.6 | Predicted 0.6 < CDR |
|---|---|---|---|
| CDR < 0.4 | 88 | 19 | 6 |
| 0.4 < CDR < 0.6 | 2 | 66 | 22 |
| 0.6 < CDR | 8 | 13 | 101 |

Weighted Kappa=0.717
Kappa=0.675
SE of kappa=0.034
95% confidence interval: From 0.608 to 0.742

TABLE 3D

Sensitivity and Specificity for CDR 0.6 and above

| Statistic | Value | 95% CI |
|---|---|---|
| Sensitivity | 82.79% | 74.90% to 89.02% |
| Specificity | 86.21% | 80.69% to 90.63% |
| Positive Predictive Value | 78.29% | 71.70% to 83.70% |
| Negative Predictive Value | 89.29% | 84.91% to 92.51% |
| Accuracy | 84.92% | 80.56% to 88.63% |

Example 3

Disc Hemorrhage Experiments

Tables 4A shows the training data for disc hemorrhage experiments. Tables 4B and 4C show the confusion matrix used for the disc hemorrhage experiments and the results of these experiments, respectively. Table 4D and 4E show the confusion matrix used for an external dataset used in disc hemorrhage experiments and the results of these experiments.

TABLE 4A

Training data for Disc Hemorrhage Experiments

Total positive images-287 (from AREDS, SiMES, UK Biobank and other public sources)
Total negative (no disc hemorrhages)-860 images (randomly chosen from the same sources)

TABLE 4B

Confusion Matrix (with test data for model building) for Disc Hemorrhage Experiments

| | Disc Hem present (predicted) | Disc hem absent (predicted) |
|---|---|---|
| Disc hem present | 73 | 13 |
| Disc Hem absent | 33 | 225 |

TABLE 4C

Results for Disc Hemorrhage Experiments

| Statistic | Value | 95% CI |
|---|---|---|
| Sensitivity | 84.88% | 75.54% to 91.70% |
| Specificity | 87.21% | 82.51% to 91.03% |
| Positive Predictive Value | 68.87% | 61.37% to 75.49% |
| Negative Predictive Value | 94.54% | 91.28% to 96.62% |
| Accuracy | 86.63% | 82.57% to 90.04% |

TABLE 4D

Confusion Matrix (on External Dataset) for Disc Hemorrhage Experiments

| | Disc Hem present (predicted) | Disc hem absent (predicted) |
|---|---|---|
| Disc hem present | 119 | 25 |
| Disc Hem absent | 62 | 769 |

TABLE 4E

Results of External Dataset for Disc Hemorrhage Experiments

| Statistic | Value | 95% CI |
|---|---|---|
| Sensitivity | 82.64% | 75.45% to 88.44% |
| Specificity | 92.54% | 90.54% to 94.23% |
| Positive Predictive Value | 65.75% | 59.90% to 71.15% |
| Negative Predictive Value | 96.85% | 95.56% to 97.78% |
| Accuracy | 91.08% | 89.11% to 92.79% |

Example 4

Glaucoma Vs Non-Glaucoma Model Results on UK Biobank Data

Table 5 shows the experimental results of the glancoma model described herein versus a non-glaucoma model as related to the UK Biobank data. The UK Biobank data is also discussed in Appendix A included herein.

TABLE 5

Results of Glaucoma Vs Non-Glaucoma Model on UK Biobank Data

| Statistic | Value | 95% CI |
|---|---|---|
| Sensitivity | 85.00% | 70.16% to 94.29% |
| Specificity | 87.00% | 78.80% to 92.89% |
| Positive Predictive Value | 72.34% | 60.78% to 81.53% |
| Negative Predictive Value | 93.55% | 87.35% to 96.82% |
| Accuracy | 86.43% | 79.62% to 91.63% |

Example 5

Glaucoma Vs Non-Glaucoma Model Results on Origa Data

Table 6 shows theexperimental results of the glaucoma model described herein versus a non-glaucoma model as related to the ORIGA-light data. The ORIGA-light data is also discussed in Appendix A included herein.

TABLE 6

Results of Glaucoma Vs Non-Glaucoma Model on ORIGA-light Data

| Statistic | Value | 95% CI |
|---|---|---|
| Sensitivity | 89.26% | 83.15% to 93.74% |
| Specificity | 93.81% | 91.33% to 95.76% |
| Positive Predictive Value | 81.10% | 75.23% to 85.84% |
| Negative Predictive Value | 96.71% | 94.87% to 97.90% |
| Accuracy | 92.77% | 90.50% to 94.64% |

Example 6

All Features Results on UK Biobank Data

Figure 4:
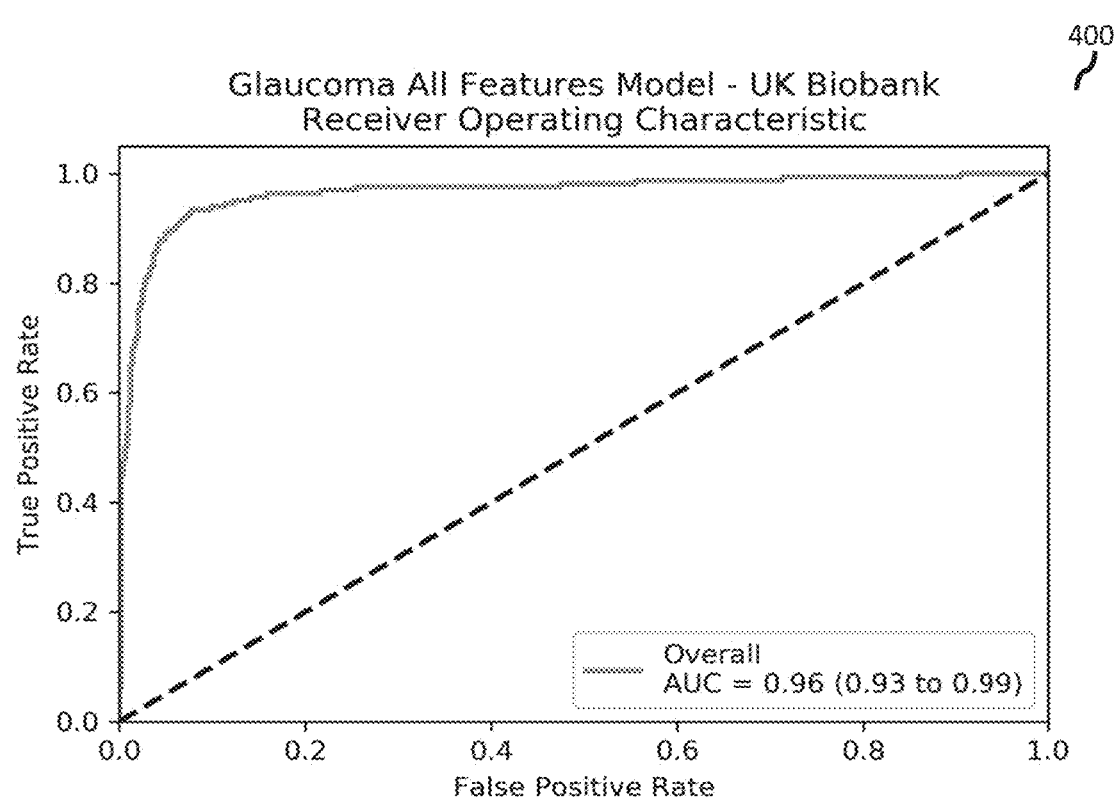
FIG. 4 depicts a graph related to the results of the all features experiments as related to UK Biobank data in terms the true positive rate versus the false positive rate according to various embodiments of the present disclosure.

Table 7 shows the experimental results of all features described herein as related to the UK Biobank data. FIG. 4 depicts a graph related to the results of the all features experiments as related to the UK Biobank data in terms the true positive rate versus the false positive rate. The UK Biobank data is also discussed in Appendix A included herein.

TABLE 7

Results of All Features Experiment on UK Biobank Data

| Statistic | Value | 95% CI |
|---|---|---|
| Sensitivity | 95.00% | 83.08% to 99.39% |
| Specificity | 94.00% | 87.40% to 97.77% |

TABLE 7-continued

Results of All Features Experiment on UK Biobank Data

| Statistic | Value | 95% CI |
|---|---|---|
| Positive Predictive Value | 86.36% | 74.40% to 93.24% |
| Negative Predictive Value | 97.92% | 92.40% to 99.45% |
| Accuracy | 94.29% | 89.05% to 97.50 |

Example 7

All Features Results on Origa-Light Data

Figure 5:
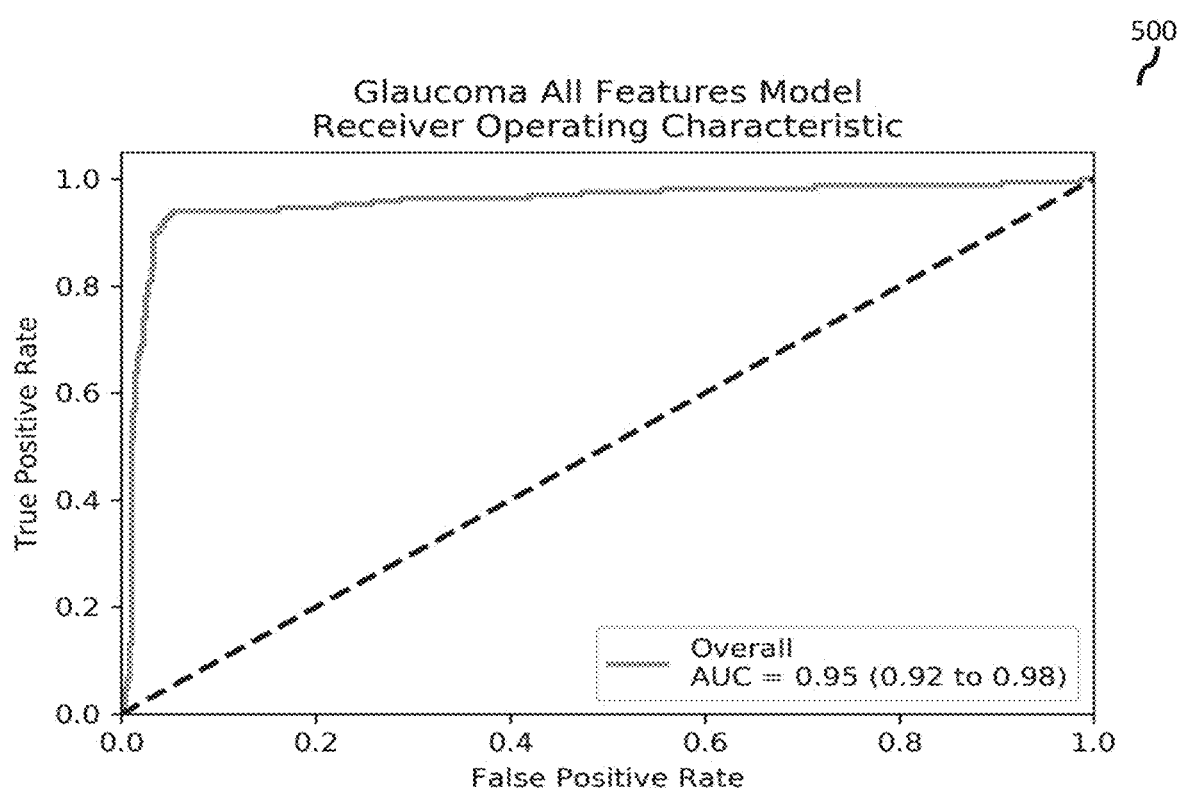
FIG. 5 depicts a graph related to the results of the all features experiments as related to ORIGA-light data in terms the true positive rate versus the false positive rate according to various embodiments of the present disclosure.
Figure 6:
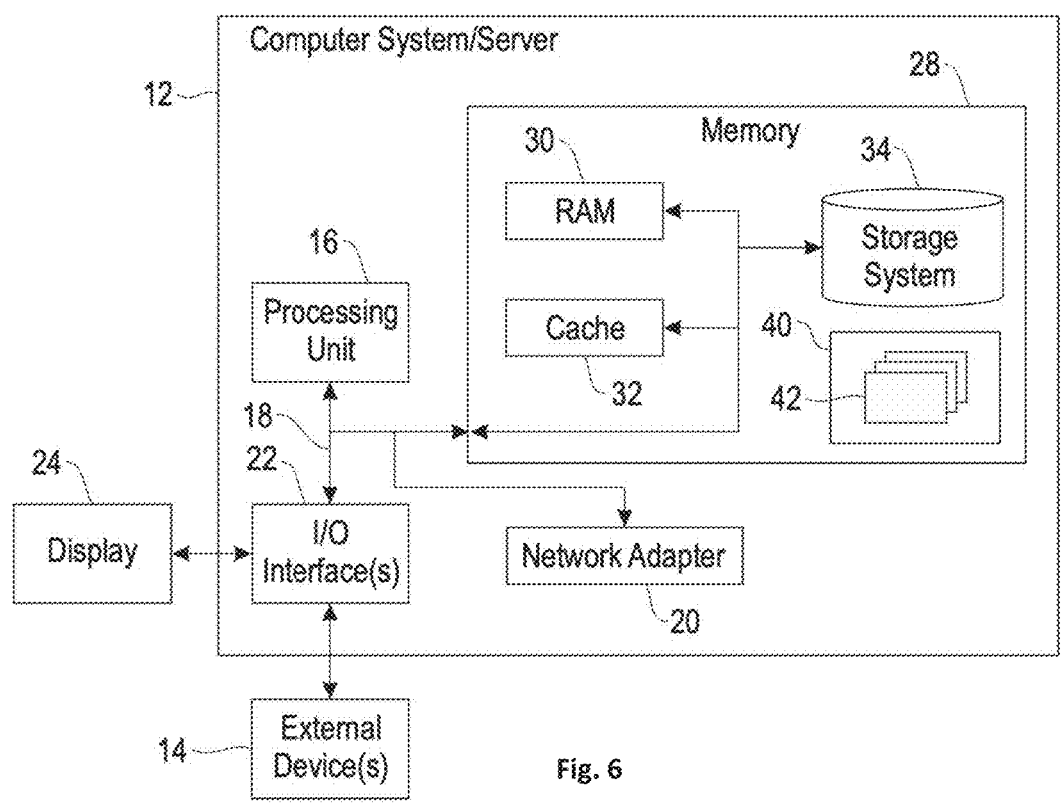
FIG. 6 depicts a computing node according to various embodiments of the present disclosure.

Table 8A shows the data split of all features described herein as related to the ORIGA-light data. Table 8B shows the predicted experimental results of all features described herein as related to the color fundus image taken from ORIGA-light data. Table 8C shows the experimental results of all features described herein as related to the ORIGA-light data. FIG. 5 depicts a graph related to the results of the all features experiments as related to the color fundus image based glaucoma detection taken from the ORIGA-light data in terms the true positive rate versus the false positive rate. The ORIGA-light data is also discussed in Appendix A included herein.

TABLE 8A

Data Split All Features Experiment on ORIGA-light Data

Data split-
Total: 648
Glaucoma: 167
No-glaucoma: 481

TABLE 8B

Predicted Results of All Features Experiment on ORIGA-light Data

| | Glaucoma (predicted) | No glaucoma (predicted) |
|---|---|---|
| Glaucoma | 156 | 11 |
| No glaucoma | 27 | 454 |

TABLE 8C

Results of All Features Experiment on ORIGA-light Data

| Statistic | Value | 95% CI |
|---|---|---|
| Sensitivity | 93.41% | 88.52% to 96.67% |
| Specificity | 94.39% | 91.94% to 96.27% |
| Positive Predictive Value | 85.25% | 79.98% to 89.31% |
| Negative Predictive Value | 97.63% | 95.89% to 98.65% |
| Accuracy | 94.14% | 92.04% to 95.82% |

TABLE 9

Results of the Glaucoma Detection Model on UK Biobank and ORIGA-light Data

| DATASET | Module | A<br>CDR | B<br>Peripapillary Atrophy | C<br>Disc Hemorrhage | D<br>Rim-disc ratio | E<br>Nasalness | F<br>Vessel Model | G<br>Sociodemographic and glaucoma risk factors<br>Multivariate of only age, race, gender, diabetes, hypertension) | Combining A, B, C, D, E, F and G*<br>*Without G<br>Proposed Glaucoma screening system | Combining A, B, C, D, E, F and G*<br>*With G<br>Proposed Glaucoma screening system |
|---|---|---|---|---|---|---|---|---|---|---|
| UK BIOBANK | Sensitivity (for glaucoma detection) | 81.97% (70.02% to 90.64%) | 36.07% (24.16% to 49.37%) | 44.26% (31.55% to 57.55%) | 83.61% (71.91% to 91.85%) | 78.69% (66.32% to 88.14%) | 55.74% (42.45% to 68.45%) | 65.57% (52.31% to 77.27%) | 88.52% (77.78% to 95.26%) | 90.16% (79.81% to 96.30%) |
| | Specificity (for glaucoma detection) | 75.00% (65.34% to 83.12%) | 94.00% (87.40% to 97.77%) | 83.00% (74.18% to 89.77%) | 77.00% (67.51% to 84.83%) | 73.00% (63.20% to 81.39%) | 54.00% (43.74% to 64.02%) | 56.00% (45.72% to 65.92%) | 94.00% (87.40% to 97.77%) | 94.00% (87.40% to 97.77%) |
| | Positive Predictive Value | 66.67% (58.27% to 74.12%) | 78.57% (61.17% to 89.51%) | 61.36% (48.65% to 72.70%) | 68.92% (60.37% to 76.35%) | 64.00% (55.67% to 71.59%) | 42.50% (35.19% to 50.15%) | 47.62% (40.57% to 54.76%) | 90.00% (80.47% to 95.16%) | 90.16% (80.77% to 95.24%) |
| | Negative Predictive Value | 87.21% (79.78% to 92.18%) | 70.68% (66.48% to 74.55%) | 70.94% (65.74% to 75.64%) | 88.51% (81.22% to 93.20%) | 84.88% (77.36% to 90.22%) | 66.67% (58.87% to 73.65%) | 72.73% (64.41% to 79.71%) | 93.07% (86.97% to 96.43%) | 94.00% (87.98% to 97.11%) |
| | Accuracy | 77.64% (70.41% to 83.82%) | 72.05% (64.44% to 78.83%) | 68.32% (60.54% to 75.42%) | 79.50% (72.44% to 85.45%) | 75.16% (67.74% to 81.62%) | 54.66% (46.63% to 62.51%) | 59.63% (51.62% to 67.28%) | 91.93% (86.59% to 95.63%) | 92.55% (87.34% to 96.09%) |
| ORIGA-light | Sensitivity (for glaucoma detection) | 77.50% (61.55% to 89.16%) | 60.00% (43.33% to 75.14%) | 57.50% (40.89% to 72.96%) | 90.00% (76.34% to 97.21%) | 90.00% (76.34% to 97.21%) | 45.00% (29.26% to 61.51%) | n/a | 95.00% (83.08% to 99.39%) | n/a |
| | Specificity (for glaucoma detection) | 80.00% (70.82% to 87.33%) | 82.00% (73.05% to 88.97%) | 61.00% (50.73% to 70.60%) | 91.00% (83.60% to 95.80%) | 91.00% (83.60% to 95.80%) | 71.00% (61.07% to 79.64%) | n/a | 94.00% (87.40% to 97.77%) | n/a |
| | Positive Predictive Value | 60.78% (50.30% to 70.36%) | 57.14% (44.99% to 68.49%) | 37.10% (29.11% to 45.86%) | 80.00% (68.02% to 88.27%) | 80.00% (68.02% to 88.27%) | 38.30% (28.16% to 49.57%) | n/a | 86.36% (74.40% to 93.24%) | n/a |
| | Negative Predictive Value | 89.89% (83.22% to 94.09%) | 83.67% (77.62% to 88.34%) | 78.21% (70.78% to 84.17%) | 95.79% (89.96% to 98.30%) | 95.79% (89.96% to 98.30%) | 76.34% (70.36% to 81.44%) | n/a | 97.92% (92.40% to 99.45%) | n/a |
| | Accuracy | 79.29% (71.62% to 85.67%) | 75.71% (67.75% to 82.56%) | 60.00% (51.39% to 68.18%) | 90.71% (84.64% to 94.96%) | 90.71% (84.64% to 94.96%) | 63.57% (55.02% to 71.53%) | n/a | 94.29% (89.05% to 97.50%) | n/a |

TABLE 10

Results of Papilledema Detection on AREDS, SiMES and UK Biobank Data

| Statistic | Value | 95% CI |
|---|---|---|
| Sensitivity | 85.00% | 62.11% to 96.79% |
| Specificity | 82.50% | 67.22% to 92.66% |
| Positive Predictive Value | 70.83% | 54.73% to 82.99% |
| Negative Predictive Value | 91.67% | 79.33% to 96.93% |
| Accuracy | 83.33% | 71.48% to 91.71% |

TABLE 11

Results of AVN Detection on Fundus Images

| Statistic | Value | 95% CI |
|---|---|---|
| Sensitivity | 88.89% | 73.94% to 96.89% |
| Specificity | 93.75% | 84.76% to 98.27% |
| Positive Likelihood Ratio | 14.22 | 5.47 to 36.99 |
| Negative Likelihood Ratio | 0.12 | 0.05 to 0.30 |
| Disease prevalence | 36.00% | 26.64% to 46.21% |
| Positive Predictive Value | 88.89% | 75.46% to 95.41% |
| Negative Predictive Value | 93.75% | 85.59% to 97.43% |
| Accuracy | 92.00% | 84.84% to 96.48% |

TABLE 12

Results of FN Detection on Fundus Images

| Statistic | Value | 95% CI |
| --- | --- | --- |
| Sensitivity | 83.78% | 67.99% to 93.81% |
| Specificity | 94.92% | 85.85% to 98.94% |
| Positive Likelihood Ratio | 16.48 | 5.42 to 50.08 |
| Negative Likelihood Ratio | 0.17 | 0.08 to 0.36 |
| Disease prevalence | 38.54% | 28.78% to 49.03% |
| Positive Predictive Value | 91.18% | 77.27% to 96.91% |
| Negative Predictive Value | 90.32% | 81.74% to 95.11% |
| Accuracy | 90.62% | 82.95% to 95.62% |

TABLE 13

Results Combined AVN and FN Detection on External Dataset

| Statistic | Value | 95% CI |
| --- | --- | --- |
| Sensitivity | 92.86% | 76.50% to 99.12% |
| Specificity | 90.00% | 78.19% to 96.67% |
| Positive Likelihood Ratio | 9.29 | 4.02 to 21.46 |
| Negative Likelihood Ratio | 0.08 | 0.02 to 0.30 |
| Disease prevalence | 35.90% | 25.34% to 47.56% |
| Positive Predictive Value | 83.87% | 69.23% to 92.32% |
| Negative Predictive Value | 95.74% | 85.51% to 98.85% |
| Accuracy | 91.03% | 82.38% to 96.32% |

Appendix a: Data Sources

UK Biobank

UK Biobank [2] has involved the collection of extensive baseline questionnaire data, physical measurements and biological samples from 500,000 men and women aged 40-69 at baseline between 2006 and 2010 in 22 centers across the UK. In the on-going study, it re-contacted subjects to the follow up information. Out of this large and popular dataset, subjects who had the follow up data were chosen.

This large open access database has enabled large studies on socio-demographic and epidemiological associations for an extensive range of health-related outcomes and conditions. Ocular data collection in UK Biobank commenced in September 2009. Acquisition of OCT images and retinal photography began in December 2009. The methods and protocol for the ocular examination component of UK Biobank were designed by ophthalmologists from Moorfields Eye Hospital, London, UK. Written, informed consent was obtained for all participants in UK Biobank. OCT images were acquired using Spectral Domain OCT device (3D OCT-1000 Mark II). This system has an axial resolution of 6 µm and an image acquisition speed of 18,000 A-scans per second (each A-scan is the measurement of the reflectance profile along the optical axis within the retina). OCT images were obtained using a raster scan protocol, 6 mm×6 mm in area, centered on the fovea. This raster scan consisted of 128 B-scans, each composed of 512 A-scans (a B-scan is a two-dimensional, cross-sectional image of retinal tissue). Using this protocol, a whole macular 3D volume of 512 A-scans by 128 B-scans is obtained in 3.6 seconds (512*128/18000).

Age-Related Eye Disease Study (AREDS)

AREDS is a major clinical trial sponsored by the National Eye Institute. AREDS participants were 55 to 80 years old at enrollment, and they had to be free of any illness or condition that would make a long-term follow-up or compliance with study medications unlikely. Based on fundus photographs graded by a central reading center, the best-corrected visual acuity, and ophthalmologic evaluations, 4,753 participants were enrolled in one of several AMD categories, including persons with no AMD. Subjects were randomly assigned to the vitamins and mineral supplements and placebo groups.

AREDS participants were assigned to four categories based on the size and extent of drusen and other AMD lesions: Normal, Early, Intermediate, and Advanced or Late AMD. These assignments were made for the left and right eyes individually. Deidentified AREDS data was used in this study and was approved by the National Eye Institute Data Access Committee, National Institute of Health.

ImageNet

Pre-trained networks helped greatly when dealing with smaller datasets. The efficientNetB4 architecture used in this experiment pretrained on the popular ImageNet dataset. The ImageNet [3] project is a large visual database designed for use in visual object recognition software research. The subset of ImageNet used for pretraining the architecture has more than 1 million images with 1000 categories. These images have been hand-annotated for the classes and categories by the project.

Refuge

REFUGE dataset part of one of the first open challenges focused on glaucoma classification and optic disc/cup segmentation from color fundus photographs. The challenge consisted of two primary tasks, namely optic disc/cup segmentation and glaucoma classification. As part of REFUGE, the dataset is publicly released including 1200 fundus images with ground truth segmentations and clinical glaucoma labels.

ORIGA-Light

The ORIGA-light dataset [4] is an ophthalmic reference image database specifically designed for glaucoma analysis. ORIGA-light serves as a benchmarking resource for researchers to evaluate image processing algorithms that detect and analyze various image signs highly related to glaucoma diagnosis. To facilitate this, the authors of ORIGA used their in-house grading tools to grade several glaucoma-related signs. The publicly available dataset that we used has 650 graded images, out of which 460 are healthy and the rest are graded as glaucoma, taken from adults aged between 40 and 80 years. Each image is segmented and annotated by trained professionals from the Singapore Eye Research Institute.

It should be understood that the foregoing description is only illustrative of the present disclosure. Various alternatives and modifications can be devised by those skilled in the art without departing from the disclosure. Accordingly, the present disclosure is intended to embrace all such alternatives, modifications, and variances. The aspects described with reference to the attached drawing figures are presented only to demonstrate certain examples of the disclosure. Other elements, steps, methods, and techniques that are insubstantially different from those described above and/or in the appended claims are also intended to be within the scope of the disclosure.

REFERENCES

ADDIN EN.REFLIST [1] M. Tan and Q. V. Le, "Efficientnet: Rethinking model scaling for convolutional neural networks," arXiv preprint arXiv: 1905.11946, 2019.

[2] C. Sudlow et al., "UK biobank: an open access resource for identifying the causes of a wide range of complex diseases of middle and old age," PLOS medicine, vol. 12, no. 3, p. e1001779, 2015.

[3] J. Deng, W. Dong, R. Socher, L.-J. Li, K. Li, and L. Fei-Fei, "Imagenet: A large-scale hierarchical image database," in 2009 IEEE conference on computer vision and pattern recognition, 2009: Ieee, pp. 248-255.

[4] Z. Zhang et al., "Origa-light: An online retinal fundus image database for glaucoma analysis and research," in 2010 Annual International Conference of the IEEE Engineering in Medicine and Biology, 2010: IEEE, pp. 3065-3068.

What is claimed is:

1. A method of detecting glaucoma, the method comprising: pre-training at least one neural network model of a plurality of neural network models using a dataset, the pre-training including: generating a plurality of vectors based on eye image variations within the dataset, wherein each vector includes a plurality of labels designating eye conditions; assigning a class label to each vector based on the plurality of labels; and generating a glaucoma-specific pre-trained model based on the assigned class labels; training the plurality of neural network models based on a plurality of indications of glaucoma based on retinal data; simultaneously generating a risk score associated with each of the plurality of indications based on the trained plurality of neural network models; combining the risk score associated with each of the plurality of indications, a socio-demographic parameter, and a presence of diabetes as a feature vector, based on a classification model, generating a probability score of glaucoma based on the feature vector, using the trained plurality of neural network models; producing based on the probability score a likelihood of glaucoma; and determining whether glaucoma is present based on the likelihood of glaucoma.

2. The method of claim 1, wherein the socio-demographic parameter includes at least one of age, gender, or race.

3. The method of claim 1, wherein the plurality of indications of glaucoma include at least two of a peripapillary atrophy value, a disc hemorrhage value, a blood vessel structure analysis value, a cup-disk ratio, a rim-to-disc ratio, a nasalness value, and a retinal entire image value.

4. The method of claim 1, wherein the risk score associated with each of the plurality of indications includes at least one continuous probability value.

5. The method of claim 1, wherein the classification model is a logistic model tree (LMT).

6. The method of claim 1, further comprising:
producing a report indicating that glaucoma is not present; and
automatically scheduling a follow-up screening within a designated time period.

7. The method of claim 1, further comprising:
producing a report indicating that glaucoma is present; and
automatically supplying a referral to a glaucoma specialist.

8. A system comprising: a computing node comprising a computer readable storage medium having program instructions embodied therewith, the program instructions executable by a processor of the computing node to cause the processor to perform a method comprising: pre-training at least one neural network model of a plurality of neural network models using a dataset, the pre-training including: generating a plurality of vectors based on eye image variations within the dataset, wherein each vector includes a plurality of labels designating eye conditions; assigning a class label to each vector based on the plurality of labels; and generating a glaucoma-specific pre-trained model based on the assigned class labels; training the plurality of neural network models based on a plurality of indications of glaucoma based on retinal data; simultaneously generating a risk score associated with each of the plurality of indications based on the trained plurality of neural network models; combining the risk score associated with each of the plurality of indications based on a classification model to produce a combined risk score; combining the risk score associated with each of the plurality of indications, a socio-demographic parameter, and a presence diabetes as a feature vector, based on a classification model, generating a probability score of glaucoma based on the feature vector, using the trained plurality of neural network models; producing based on the probability score a likelihood of glaucoma; and determining whether glaucoma is present based on the likelihood of glaucoma.

9. The system of claim 8, wherein the socio-demographic parameter includes at least one of age, gender, or race.

10. The system of claim 8, wherein the plurality of indications of glaucoma further include at least two of a peripapillary atrophy value, a disc hemorrhage value, a blood vessel structure analysis value, a cup-disk ratio, a rim-to-disc ratio, a nasalness value, and a retinal entire image value.

11. The system of claim 8, wherein the risk score associated with each of the plurality of indications includes at least one continuous probability value.

12. The system of claim 8, wherein the classification model is a logistic model tree (LMT).

13. The system of claim 8, wherein the method further comprises:
producing a report indicating that glaucoma is not present; and
automatically scheduling a follow-up screening within a designated time period.

14. The system of claim 8, wherein the method further comprises:
producing a report indicating that glaucoma is present; and
automatically supplying a referral to a glaucoma specialist.

15. A non-transitory computer-readable medium storing instructions that, when executed by a processor, cause the processor to perform a method for backing up and restoring a cluster of nodes, the method comprising: pre-training at least one neural network model of a plurality of neural network models using a dataset, the pre-training including: generating a plurality of vectors based on eye image variations within the dataset, wherein each vector includes a plurality of labels designating eye conditions; assigning a class label to each vector based on the plurality of labels; and generating a glaucoma-specific pre-trained model based on the assigned class labels; training the plurality of neural network models based on a plurality of indications of glaucoma based on retinal data; simultaneously generating a risk score associated with each of the plurality of indications based on the trained plurality of neural network models; combining the risk score associated with each of the plurality of indications, a socio-demographic parameter, and a presence of diabetes as a feature vector, based on a classification model, generating a probability score of glaucoma based on the feature vector, using the trained plurality of neural network models; producing based on the probability score a likelihood of glaucoma; and determining whether glaucoma is present based on the likelihood of glaucoma.

16. The non-transitory computer-readable medium of claim 15, wherein the socio-demographic parameter includes at least one of age, gender, or race.

17. The non-transitory computer-readable medium of claim 15, wherein the plurality of indications of glaucoma further include at least two of a peripapillary atrophy value, a disc hemorrhage value, a blood vessel structure analysis value, a cup-disk ratio, a rim-to-disc ratio, a nasalness value, and a retinal entire image value.

18. The non-transitory computer-readable medium of claim 15, wherein the method further comprises:
  producing a report indicating that glaucoma is not present; and
  automatically scheduling a follow-up screening within a designated time period.

19. The non-transitory computer-readable medium of claim 15, wherein the method further comprises:
  producing a report indicating that glaucoma is present; and
  automatically supplying a referral to a glaucoma specialist.

\* \* \* \* \*